(12) United States Patent
Howitt et al.

(10) Patent No.: US 10,119,169 B2
(45) Date of Patent: Nov. 6, 2018

(54) METHODS TO DIAGNOSE AND TREAT MULLERIAN ADENOSARCOMA

(71) Applicant: The Brigham and Women's Hospital, Inc., Boston, MA (US)

(72) Inventors: Brooke Howitt, Jamaica Plain, MA (US); Bradley Quade, Norwood, MA (US); Marisa Nucci, Brookline, MA (US); Lynette Sholl, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 268 days.

(21) Appl. No.: 14/685,292

(22) Filed: Apr. 13, 2015

(65) Prior Publication Data

US 2015/0322521 A1 Nov. 12, 2015

Related U.S. Application Data

(60) Provisional application No. 61/978,353, filed on Apr. 11, 2014, provisional application No. 61/978,243, filed on Apr. 11, 2014.

(51) Int. Cl.

| *C12Q 1/68* | (2018.01) |
| *C12P 19/34* | (2006.01) |
| *C12Q 1/6886* | (2018.01) |
| *C12Q 1/6883* | (2018.01) |

(52) U.S. Cl.
CPC ......... *C12Q 1/6886* (2013.01); *C12Q 1/6883* (2013.01); *C12Q 2600/106* (2013.01); *C12Q 2600/156* (2013.01)

(58) Field of Classification Search
None
See application file for complete search history.

(56) References Cited

PUBLICATIONS

Slonin, Nature Genetics Supplement, vol. 32, Dec. 2002, pp. 502-508.*
Michiels et al. Lancet, 2005; 365:488-492.*
Hegele (Arterioscler. Thromb. Vasc. Biol, 2002, 22; 1058-1061.*
Ionnidis (Plost Med, 2005, 2(8):e124).*
Juppner, Bone, vol. 17, Aug. 1995, 39S-42S.*
Cooke (Oncogene, 2010, vol. 29, 4905-4913).*
Mittal (Modern Pathology, 2009, 22, 1303-1311).*
Abeler and Nenodovic, "Diagnostic Immunohistochemistry in Uterine Sarcomas: A Study of 397 Cases," Int. J. Gynecol. Pathol., May 2011, 30:236-243.
Abeler et al., "Uterine sarcomas in Norway. A histopathological and prognostic survey of a total population from 1970 to 2000 including 419 patients," Histopathology, Feb. 2009, 54(3):355-364.
Amant et al., "Immunohistochemical Determination of Estrogen and Progesterone Receptor Positivity in Uterine Adenosarcoma," Gynecol. Oncol., Jun. 2004, 93:680-685.
Amant et al., "Immunohistochemical Expression of Cd10 Antigen in Uterine Adenosarcoma," Int. J. Gynecol. Cancer, 2004, 14:1118-1121.
Anderson et al., "P53, Epidermal Growth Factor, and Platelet-Derived Growth Factor in Uterine Leiomyosarcoma and Leiomyomas," Int. J. Gynecol. Cancer, 2006, 16:849-853.
Auerbach et al., "Malignant Mixed Mullerian Tumors of the Uterus. An Immunohistochemical Study," Int. J. Gynecol. Pathol., May 1988, 7:123-130.
Bernard et al., "Uterine Adenosarcomas: A Dual-Institution Update on Staging, Prognosis and Survival," Gynecol., Oncol., Dec. 2013, 131:634-639.
Blom and Guerrieri, "Adenosarcoma of the Uterus: A Clinicopathologic, DNA Flow Cytometric, P53 and Mdm-2 Analysis of 11 Cases," Int. J. Gynecol. Cancer, Jan. 1999, 9:37-43.
Bol et al., "An Endometrial Polyp with a Rearrangement of Hmgi-C Underlying a Complex Cytogenetic Rearrangement Involving Chromosomes 2 and 12," Cancer Genet. Cytogenet., Aug. 1996, 90:88-90.
Boo et al., "High Mobility Group A2 Potentiates Genotoxic Stress in Part through the Modulation of Basal and DNA Damage-Dependent Phosphatidylinositol 3-Kinase-Related Protein Kinase Activation," Cancer Res., Aug. 2005, 65:6622-6630.
Cerami et al., "The cBio Cancer Genomics Portal: An Open Platform for Exploring Multidimensional Cancer Genomics Data," Cancer Discovery, May 2012, 2:401.
Chen et al., "Molecular Cytogenetic Characterization of a Case of Mullerian Adenosarcoma," Cancer Genet. Cytogenet., Jan. 2004, 148:129-132.
Chiang and Oliva, "Cytogenetic and molecular aberrations in endometrial stromal tumors," Hum. Pathol., May 2011, 42(5):609-617.
Clappier et al., "The C-MYB locus is involved in chromosomal translocation and genomic duplications in human T-cell acute leukemia (T-ALL), the translocation defining a new T-ALL subtype in very young children," Blood, Aug. 2007, 110(4):1251-1261.
Clement and Scully, "Mullerian Adenosarcoma of the Uterus. A Clinicopathologic Analysis of Ten Cases of a Distinctive Type of Mullerian Mixed Tumor," Cancer, 1974, 34:1138-1149.
Clement and Scully, "Mullerian Adenosarcoma of the Uterus: A Clinicopathologic Analysis of 100 Cases with a Review of the Literature," Hum. Pathol., Apr. 1990, 21:363-381.
Clement, "Mullerian adenosarcomas of the uterus with sarcomatous overgrowth. A clinicopathological analysis of 10 cases," Am. J. Surg. Pathol., Jan. 1989, 13(1):28-38.
Clement and Scully, "Extrauterine mesodermal (mullerian) adenosarcoma: a clinicopathologic analysis of five cases." Am. J. Clin. Pathol., Mar. 1978, 69(3):276-283.
D'Angelo and Prat, "Uterine sarcomas: a review," Gynecol. Oncol., Jan. 2010, 116(1):131-9.
Dal Cin et al., "Rearrangement of 12q14-15 in Pulmonary Chondroid Hamartoma," Genes Chromosomes Cancer, Oct. 1993, 8:131-133.
Dal Cin et al., "Genomic Changes in Endometrial Polyps Associated with Tamoxifen Show No Evidence for Its Action as an External Carcinogen," Cancer Res., Jun. 1998, 58:2278-2281.

(Continued)

*Primary Examiner* — Sarae L Bausch
(74) *Attorney, Agent, or Firm* — Fish & Richardson P.C.

(57) ABSTRACT

Methods for diagnosing and treating Müllerian Adenosarcoma that include detecting the presence of one or more of a mutation in an ATRX gene, and/or a Copy Number Variation (CNV) in a MYBL1, MDM2, HMGA2, and/or CDK4 gene.

5 Claims, 14 Drawing Sheets

(56) References Cited

PUBLICATIONS

Dal Cin et al., "Consistent Involvement of Band 12q14 in Two Different Translocations in Three Lipomas from the Same Patient," Cancer Genet. Cytogenet., Apr. 1988, 31:237-240.
Dal Cin et al., "Involvement of 6p in an Endometrial Polyp," Cancer Genet. Cytogenet., 1991, 51:279-280.
Dal Cin et al., "Four Cytogenetic Subgroups Can Be Identified in Endometrial Polyps," Cancer Res., Apr. 1995, 55:1565-1568.
Dal Cin et al., "Amplification and Expression of the Hmgic Gene in a Benign Endometrial Polyp," Genes Chromosomes Cancer, Jun. 1998, 22:95-99.
De Wilde et al., "Loss of Atrx or Daxx Expression and Concomitant Acquisition of the Alternative Lengthening of Telomeres Phenotype Are Late Events in a Small Subset of Men-1 Syndrome Pancreatic Neuroendocrine Tumors," Mod. Pathol., 2012, 25:1033-1039.
Dei Tos et al., "Molecular Abnormalities of the P53 Pathway in Dedifferentiated Liposarcoma," J. Pathol., Jan. 1997, 181:8-13.
Dewaele et al., "Identification of a novel, recurrent MBTD1-CXorf67 fusion in low-grade endometrial stromal sarcoma." Int. J. Cancer, 2013, 134(5):1112-22.
Eichhorn et al., "Mesodermal (Mullerian) Adenosarcoma of the Ovary: A Clinicopathologic Analysis of 40 Cases and a Review of the Literature," Am. J. Surg. Pathol., Oct. 2002, 26:1243-1258.
FIGO Committee on Gynecologic Oncology, "FIGO staging for uterine sarcomas," Int. J. Gynecol. Obstetrics, 2009, 104:179.
Fox, "Mullerian Adenosarcoma of the Uterine Body: A Report of Nine Cases," Histopathology, May 1979, 3:167-180.
Gallardo and Prat Mullerian Adenosarcoma: A Clinicopathologic and Immunohistochemical Study of 55 Cases Challenging the Existence of Adenofibroma. Am. J. Surg. Pathol., Feb. 2009, 33:278-288.
Gao et al., "Integrative Analysis of Complex Cancer Genomics and Clinical Profiles Using the cBioPortal," Sci. Signal, Apr. 2013, 6(269):p. 11.
Garcia et al., "Development and Clinical Validation of a Targeted Next-Generation Sequencing Platform for the Detection of Somatic Mutations, Indels, Rearrangements, and Copy-Number Alterations in Human Tumors," The Journal of Molecular Diagnostics, 2013, 15:872.
Gollard et al., "Two Unusual Presentations of Mullerian Adenosarcoma: Case Reports, Literature Review, and Treatment Considerations," Gynecol. Oncol., Dec. 1995, 59:412-422.
Hammond et al., "American Society of Clinical Oncology/College of American Pathologists Guideline Recommendations for Immunohistochemical Testing of Estrogen and Progesterone Receptors in Breast Cancer," Journal of Clinical Oncology, Jun. 2010, 28(16):2784-2795.
Howitt et al., "Uterine polyps with features overlapping with those of Müllerian adenosarcoma: a clinicopathologic analysis of 29 cases emphasizing their likely benign nature," Am. J. Surg. Pathol., Jan. 2015, 39(1):116-26.
Ito et al., "Comprehensive Mapping of P53 Pathway Alterations Reveals an Apparent Role for Both Snp309 and Mdm2 Amplification in Sarcomagenesis," Clin. Cancer Res., Feb. 2011, 17:416-426.
Jiao et al., "Frequent Atrx, Cic, Fubp1 and Idh1 Mutations Refine the Classification of Malignant Gliomas," Oncotarget, 2012, 3:709-722.
Jiao et al., "Daxx/Atrx, Men1, and Mtor Pathway Genes Are Frequently Altered in Pancreatic Neuroendocrine Tumors," Science, Mar. 2011, 331:1199-1203.
Jones and Lefkowitz, "Adenosarcoma of the uterine cervix: a clinicopathological study of 12 cases," Int J Gynecol Pathol, Jul. 1995, 14(3):223-229.
Kaku et al., "Adenosarcoma of the Uterus: A Gynecologic Oncology Group Clinicopathologic Study of 31 Cases," Int. J. Gynecol. Pathol., 1992, 11:75-88.
Laxman et al., "Cytogenetic profile of uterine sarcomas," Cancer, Feb. 1993, 71(4):1283-1288.
Liu et al., "Mutation and Overexpression of the P53 Tumor Suppressor Gene Frequently Occurs in Uterine and Ovarian Sarcomas," Obstet. Gynecol., 1994, 83:118-124.
Maekawa et al., "Delta1-Notch3 Interactions Bias the Functional Differentiation of Activated Cd4+ T Cells," Immunity, Oct. 2003, 19:549-559.
Major et al., "Prognostic factors in early-stage uterine sarcoma. A Gynecologic Oncology Group study," Cancer, Feb. 1993, 71:1702-1709.
Manoharan et al., "Mullerian Adenosarcoma of Uterine Cervix: Report of Three Cases and Review of Literature," Gynecol. Oncol., Apr. 2007, 105:256-260.
Marinoni et al., "Loss of Daxx and Atrx Are Associated with Chromosome Instability and Reduced Survival of Patients with Pancreatic Neuroendocrine Tumors," Gastroenterology, Feb. 2014, 146:453-460 e455.
McCluggage, "Mullerian Adenosarcoma of the Female Genital Tract," Adv. Anat. Pathol., Mar. 2010, 17:122-129.
Medeiros et al, "Hmga1 and Hmga2 Rearrangements in Mass-Forming Endometriosis," Genes Chromosomes Cancer, 2010, 49:630-634.
Medeiros et al., "Frequency and Characterization of Hmga2 and Hmga1 Rearrangements in Mesenchymal Tumors of the Lower Genital Tract," Genes Chromosomes Cancer, Nov. 2007, 46:981-990.
Mikami et al., "Expression of Cd10 in Malignant Mullerian Mixed Tumors and Adenosarcomas: An Immunohistochemical Study," Mod. Pathol., Sep. 2002, 15:923-930.
Mitani et al., "Comprehensive analysis of the MYB-NFIB gene fusion in salivary adenoid cystic carcinoma: Incidence, variability, and clinicopathologic significance," Clin. Cancer Res., Oct. 2010, 16(19):4722-4731.
Nucci et al., "Chromosomal Translocation T(8;12) Induces Aberrant Hmgic Expression in Aggressive Angiomyxoma of the Vulva," Genes Chromosomes Cancer, Oct. 2001, 32:172-176.
Ramkissoon et al., "Genomic Analysis of Diffuse Pediatric Low-Grade Gliomas Identifies Recurrent Oncogenic Truncating Rearrangements in the Transcription Factor Mybl1," PNAS, May 2013, 110:8188-8193.
Shi et al., "The diagnosis and treatment of Mullerian adenosarcoma of the uterus," Aust. N. Z. J. Obstet. Gynaecol., Dec. 2008, 48(6):596-600.
Soslow RA, Ali A, Oliva E. Mullerian Adenosarcomas: An Immunophenotypic Analysis of 35 Cases, Am. J. Surg. Pathol., Jul. 2008, 32:1013-1021.
Speleman et al., "Is T(6;20)(P21;Q13) a Characteristic Chromosome Change in Endometrial Polyps?" Genes Chromosomes Cancer, Jul. 1991, 3:318-319.
Spencer et al., "Comparison of Clinical Targeted Next-Generation Sequence Data from Formalin-Fixed and Fresh-Frozen Tissue Specimens," J. Mol. Diagn., Sep. 2013, 15:623-633.
Sprogoe-Jakobsen and Holund, "Immunohistochemistry (Ki-67 and P53) as a Tool in Determining Malignancy in Smooth Muscle Neoplasms (Exemplified by a Myxoid Leiomyosarcoma of the Uterus)," APMIS, 1996, 104:705-708.
Swisher et al., "The Expression of Epidermal Growth Factor Receptor, Her-2/Neu, P53, and Ki-67 Antigen in Uterine Malignant Mixed Mesodermal Tumors and Adenosarcoma," Gynecol. Oncol., Jan. 1996, 60:81-88.
Tallini et al., "Hmgi-C and Hmgi(Y) Immunoreactivity Correlates with Cytogenetic Abnormalities in Lipomas, Pulmonary Chondroid Hamartomas, Endometrial Polyps, and Uterine Leiomyomas and Is Compatible with Rearrangement of the Hmgi-C and Hmgi(Y) Genes.," Lab Invest, Mar. 2000, 80:359-369.
Taylor et al., "DNA Mismatch Repair and Tp53 Defects Are Early Events in Uterine Carcinosarcoma Tumorigenesis," Mod. Pathol., 2006, 19:1333-1338.
Tesfaye et al., "The High-Mobility Group A1 Gene up-Regulates Cyclooxygenase 2 Expression in Uterine Tumorigenesis," Cancer Res., May 2007, 67:3998-4004.
Van Mieghem et al., "Cd10, Estrogen and Progesterone Receptor Expression in Ovarian Adenosarcoma," Gynecol. Oncol., Nov. 2005, 99:493-496.

(56) References Cited

OTHER PUBLICATIONS

Vanni et al., "Endometrial Polyp: Another Benign Tumor Characterized by 12q13-Q15 Changes," Cancer Genet. Cytogenet., Jul. 1993, 68:32-33.
Walter et al., "Inv(12)(P11.2q13) in an Endometrial Polyp," Cancer Genet. Cytogenet., Aug. 1989, 41:99-103.
West et al., "MYB expression and translocation in adenoid cystic carcinomas and other salivary gland tumors with clinicopathologic correlation," Am. J. Surg. Pathol., Jan. 2011, 35(1):92-99.
Wu et al., "The Genomic Landscape of Diffuse Intrinsic Pontine Glioma and Pediatric Non-Brainstem High-Grade Glioma," Nat. Genet., May 2014, 46:444-450.
Zaloudek and Norris, "Adenofibroma and Adenosarcoma of the Uterus: A Clinicopathologic Study of 35 Cases," Cancer, Jul. 1981, 48:354-366.
Zhang, et al., "Whole-genome sequencing identifies genetic alterations in pediatric low-grade gliomas," Nat Genet., Jun. 2013, 45(6):602-612.
Bujnicki et al., "Inhibition of Myb-dependent gene expression by the sesquiterpene lactone mexicanin-I," Leukemia, 2011, 26: 615-702.

\* cited by examiner

FIGs. 1A-D

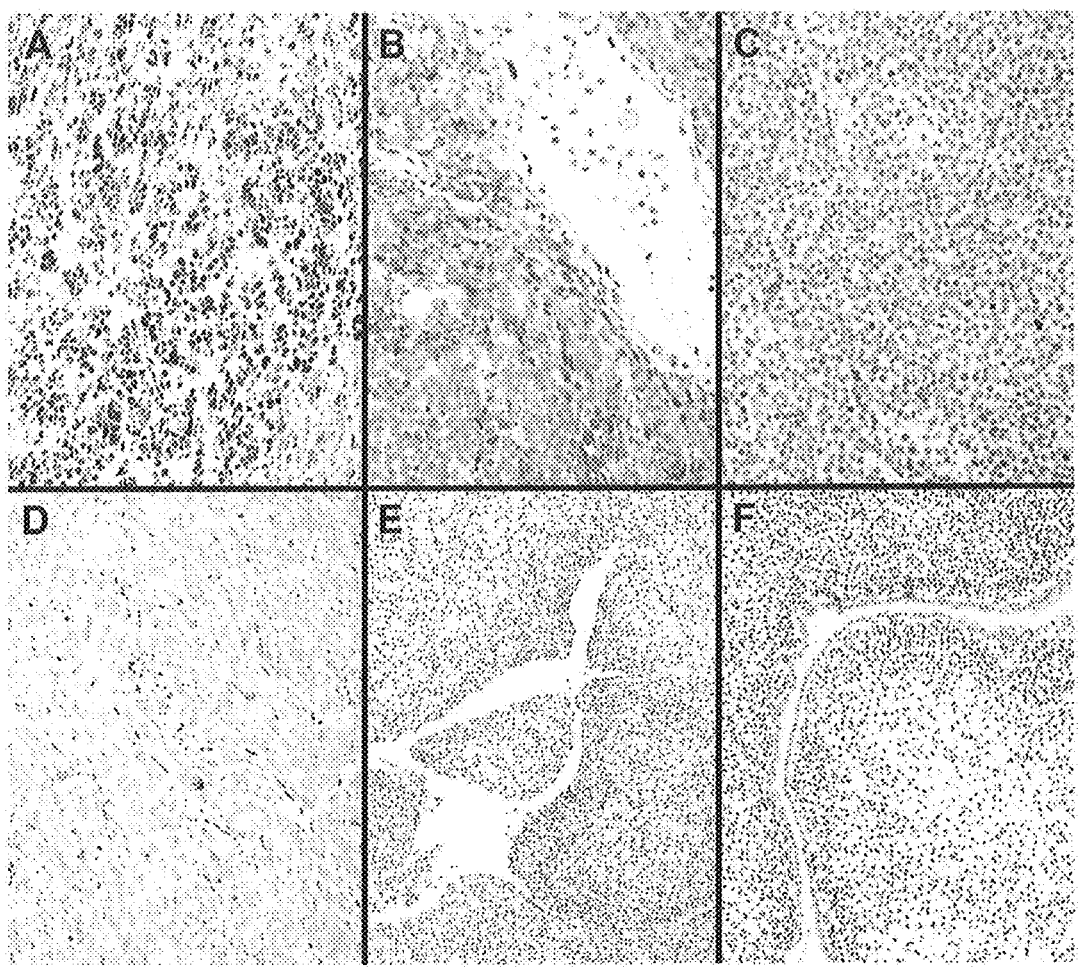
FIGs. 3A-F

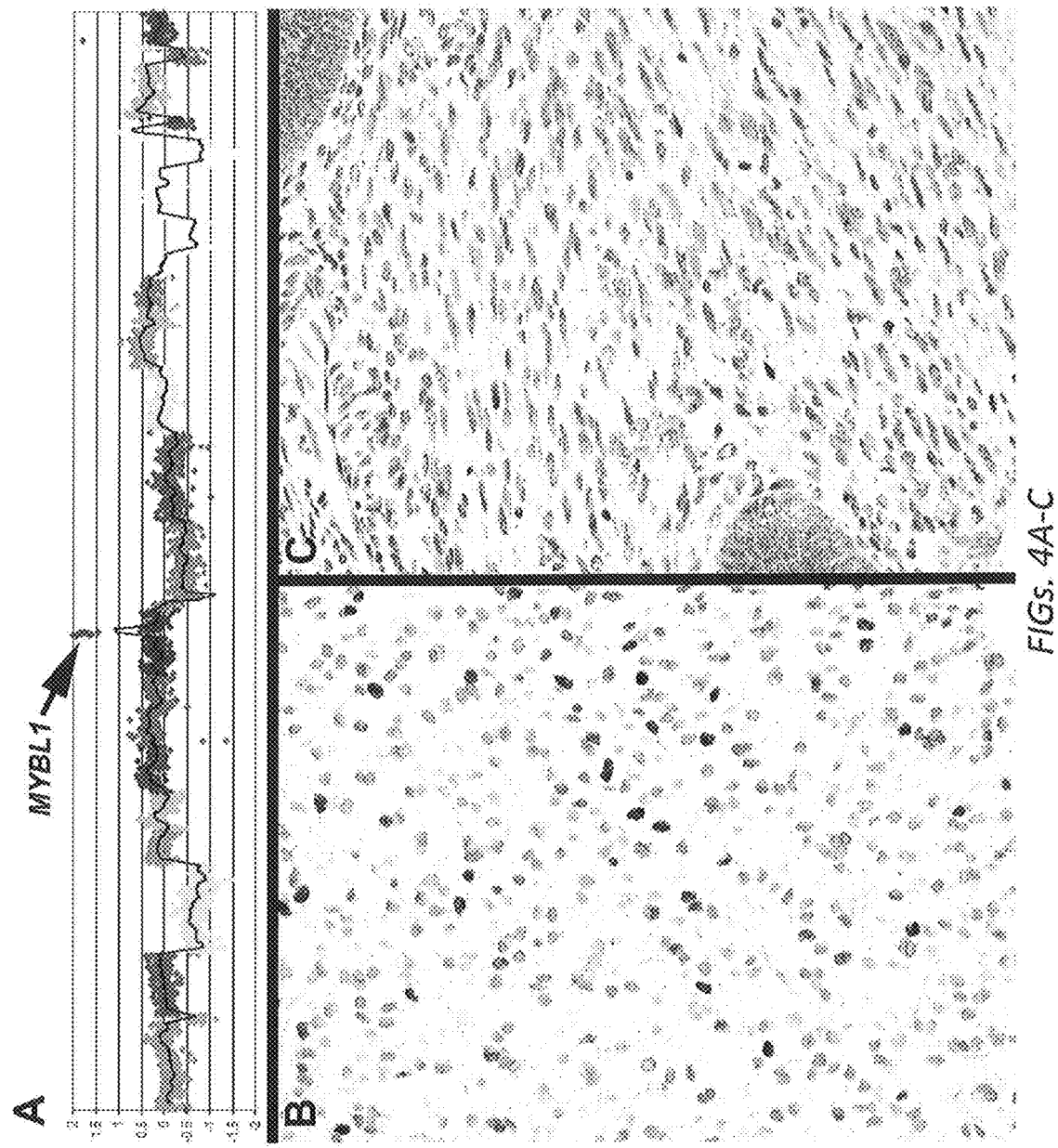
FIGs. 4A-C

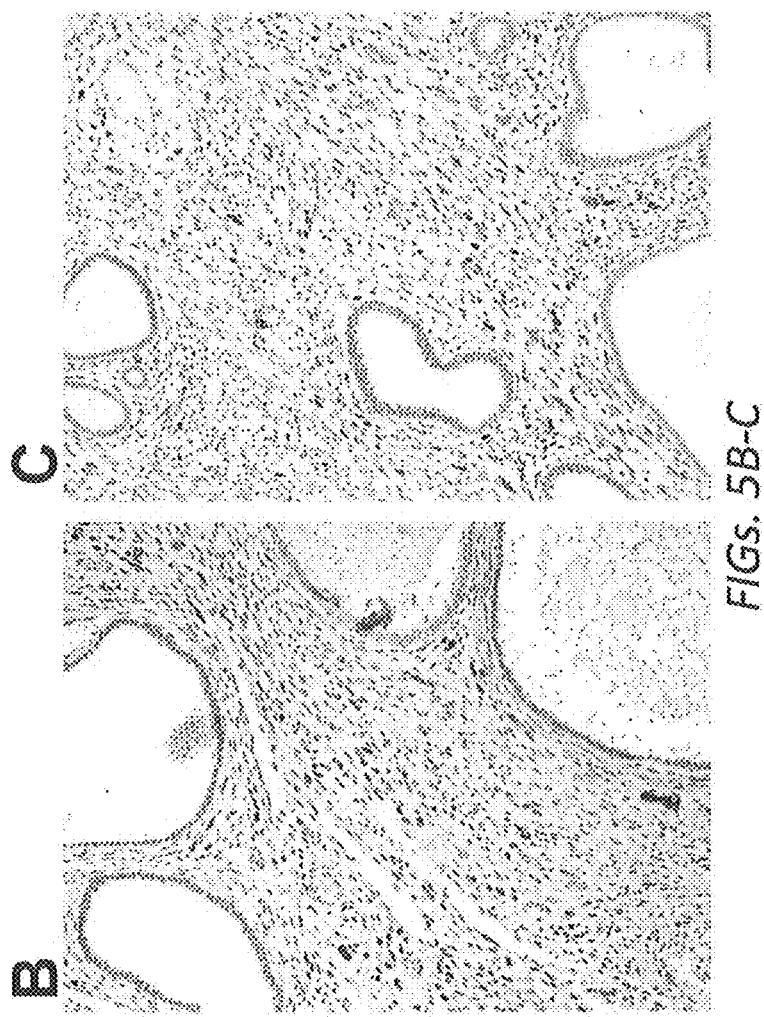
FIGs. 5B-C

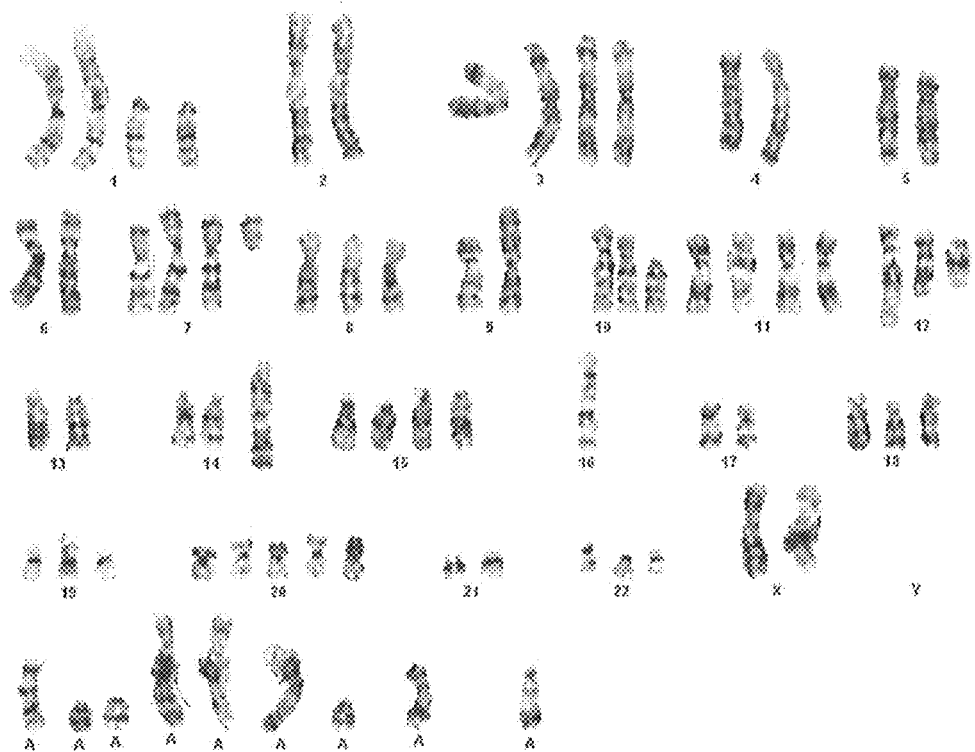
FIG. 8
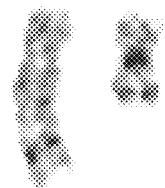  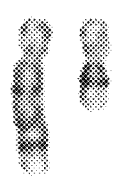
FIG. 9A              FIG. 9B

METHODS TO DIAGNOSE AND TREAT MULLERIAN ADENOSARCOMA

CLAIM OF PRIORITY

This application claims the benefit of U.S. Provisional Application Ser. Nos. 61/978,243, filed on Apr. 11, 2014, and 61/978,353, also filed on Apr. 11, 2014. The entire contents of the foregoing are incorporated herein by reference.

TECHNICAL FIELD

Described are methods for diagnosing and treating Müllerian Adenosarcoma that include detecting the presence of one or more of a mutation in an ATRX (alpha thalassemia/mental retardation syndrome X) gene, and/or a Copy Number Variation (CNV) in a MYBL1 (V-Myb Avian Myeloblastosis Viral Oncogene Homolog-Like 1), MDM2 (Mouse Double Minute 2, Human Homolog Of, also known as MDM2 proto-oncogene, E3 ubiquitin protein ligase), HMGA2 (high mobility group AT-hook 2) and/or CDK4 (cyclin-dependent kinase 4) gene.

BACKGROUND

Müllerian adenosarcoma (MA) is an uncommon biphasic neoplasm of the female genital tract, representing 5-10% of uterine mesenchymal neoplasms (Major et al. 1993, Abeler et al. 2009). MA is composed of malignant stroma and benign Müllerian epithelium (Clement and Scully 1974, Fox et al. 1979, Clement and Scully 1990). The majority of MA arise in the uterine corpus but it has also been well-described arising in the cervix, ovary, vagina, and sites outside the female genital tract (likely arising from endometriosis) (Clement and Scully 1978, Jones and Lefkowitz 1995, Eichhorn et al. 2002). Uterine MA often presents as a polypoid mass occupying the endometrial cavity, and may be multifocal. Histologically, it is characterized by well-developed, broad leaf-like glandular architecture, with peri-glandular stromal condensation, cytologic atypia, and mitoses (1-5). Although many MA are clinically indolent, the presence of sarcomatous overgrowth (SO, defined as >25% of the tumor composed of sarcoma without an epithelial component), is strongly associated with a substantial risk of recurrence and metastasis (Clement 1989, Gallardo and Prat 2009). Uterine MA lacking SO are relatively indolent, having a 20-30% recurrence rate (1, 2, 5), but low rate of distant metastasis, and low overall mortality (1, 2, 4, 5). Such tumors are treated primarily with surgery (5), whereas those with SO are often treated with chemotherapy, radiation therapy, or both. An additional histologic parameter that may indicate a worse prognosis is deep (greater than 50%) myometrial invasion (1, 2, 6, 7).

Immunohistochemically, CD10 is considered to be the most commonly recognized positive marker for MA (8-14); however, WT-1, ER, and PR are also often expressed (8-12). SMA (12-14) and desmin (12-14) are variably expressed. In MA, particularly those with SO, the proliferative index is elevated (11, 12), and frequently accompanied by loss of CD10, WT-1, PR, and ER expression (8-12). Some studies have found that p53 is aberrantly overexpressed in a few MA with SO (11, 15, 16). Despite these efforts, no reliable immunohistochemical marker distinguishes MA from potentially morphologically similar tumors, namely carcinosarcoma, endometrial stromal neoplasms, benign uterine polyps, so-called "adenofibroma," embryonal rhabdomyosarcoma, and occasionally, smooth muscle tumors. Unfortunately, there exists no known recurrent cytogenetic abnormality, or molecular diagnostic test to serve as an adjunct to the hematoxylin and eosin (H&E) based diagnosis, so presently, the diagnosis is essentially made on histologic grounds without any reliable confirmatory immunohistochemical or molecular/genetic test.

SUMMARY

The present invention is based, at least in part, on the discovery of genetic abnormalities associated with diagnosis and prognosis in Müllerian Adenosarcoma.

Thus, in a first aspect the invention provides methods for treating a subject who has a mass that is known or suspected to be Müllerian Adenosarcoma (MA). The methods include obtaining a sample comprising cells from the mass in a subject; performing an assay to detect the presence of one or more of a Copy Number Variation (CNV) in a MYBL1, MDM2, HMGA2, and/or CDK4 gene, and/or a mutation in an ATRX gene; selecting a subject who has a mutation in an ATRX gene, and/or a copy number gain in a MYBL1, MDM2, HMGA2, and/or CDK4 gene; and administering a treatment comprising one or more of: radical surgical resection, administration of radiotherapy, administration of a MYBL1 inhibitor, and administration of chemotherapy.

Also provided herein are methods for determining risk of developing MA with Sarcomatous Overgrowth (SO). The methods include obtaining a sample comprising cells from a mass in a subject that is known or suspected to have MA; performing an assay to detect the presence of one or more of a CNV in a MYBL1, MDM2, HMGA2, and/or CDK4 gene, and/or a mutation in an ATRX gene; and assigning the subject a high risk of developing MA with SO based on the presence of a CN gain in a MYBL1, MDM2, HMGA2, and/or CDK4 gene, and/or a mutation in an ATRX gene.

Further provided herein are methods for diagnosing a subject who has a mass that is known or suspected to be MA. The methods include performing an assay to detect the presence of one or more of a CNV in a MYBL1, MDM2, HMGA2, and/or CDK4 gene, and/or a mutation in an ATRX gene; and diagnosing the presence of MA in the subject who has a CN gain in a MYBL1, MDM2, HMGA2, and/or CDK4 gene, and/or a mutation in an ATRX gene.

In some embodiments, detecting the presence of a copy number gain in a MYBL1 gene comprises: determining the copy number of the MYBL1 gene in the cells; comparing the copy number of the MYBL1 gene in the cells to a reference copy number that represents a copy number in a normal cell; and detecting the presence of a copy number gain when the copy number of the MYBL1 gene in the cells is greater than the reference copy number.

In some embodiments, determining the copy number of the MYBL1 gene comprises using a method selected from the group consisting of fluorescent in-situ hybridization (FISH); gene chip hybridization; multiplexed gene expression analysis; hybridization based digital barcode quantification assays; and lysate based hybridization assays utilizing branched DNA signal amplification.

In some embodiments, the methods include administering an MYBL1 inhibitor, wherein the MYBL1 inhibitor is mexicanin I.

In some embodiments, the methods include administering chemotherapy, wherein the chemotherapy comprises administration of one or more rounds of doxorubicin and carboplatin, cyclophosphamide, vincristine and carboplatin, or dacarbazine.

In some embodiments, the mass is a uterine or cervical mass, and the radical surgical resection is radical hysterectomy or modified radical hysterectomy.

In some embodiments, the subject has not been diagnosed with MA, or has an atypical polyp, but does not have MA.

In some embodiments, the presence of a copy number gain is detected by detecting a level of MYBL1, MDM2, HMGA2, and/or CDK4 protein in the sample, e.g., by contacting the sample with antibodies that bind to MYBL1, antibodies that bind to MDM2, antibodies that bind to HMGA2, and/or antibodies that bind to CDK4, and comparing the level of MYBL1, MDM2, HMGA2, and/or CDK4 protein in the sample to a reference sample. A level of protein in the sample that is above the level of the reference is equivalent to a copy number gain in the methods described herein.

Also provided herein are methods for treating a subject who has MA, including administering a therapeutically effective amount of a MYBL1 inhibitor, e.g., Mexicanin I.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3A-F: Immunohistochemistry for p53 and ATRX in Müllerian Adenosarcoma. Overexpression of p53 was evident in one case (A; Case #18). Complete loss of p53, consistent with a "null" immunophenotype was seen in one case (B; Case #16), with positive endothelium as an internal control. The remainder of cases had scattered tumor cells positive for p53 (C). Similarly, ATRX was completely lost in tumor cells in one case (D; Case #16), with internal endothelium as a positive control, but was intact in all other cases (E) including Case #17 which harbored a missense mutation (F).

FIGS. 4A-C: MYBL1 Amplification in Müllerian Adenosarcoma. Copy number gains in MYBL1 (arrow) were identified in 4 cases (A; Case 17), displayed as the plot of copy number variation by chromosome (color-coded). The vertical axis is the ratio of number of reads for this specimen versus a panel of normals in log base 2 scale. A value of 0 denotes no difference from normal (diploid). The majority of cases with MYBL1 CNV gains strongly expressed MYBL1 in a subset of tumor cells (B), and one MA without MYBL1 copy number gains also had scattered cells positive for MYBL1 (C). All other cases were negative for MYBL1 by immunohistochemistry.

FIGS. 5A-F: MDM2, CDK4, and HMGA2 in Müllerian Adenosarcoma. Gene level copy number gains of MDM2 and CDK4 were identified in CNV analysis, with the plot of copy number variation by chromosome (color-coded). The vertical axis is the ratio of number of reads for this specimen versus a panel of normals in log base 2 scale. A value of 0 denotes no difference from normal (diploid). (A; arrow; data for chromosome 12 is shown in light grey), which correlated with increased protein expression by immunohistochemistry for CDK4 (B) and MDM2 (C). Given the location of HMGA2 between MDM2 and CDK4 (D; sequence map data including gene size and location relative to the cytogenetic map are based on human genome build hg19 (February 2009)), most MA with copy number gains in MDM2 and CDK4 also overexpressed HMGA2 by immunohistochemistry (E). MDM2 amplification was confirmed by FISH in 2 cases (F).

FIG. 8. Mullerian adenosarcoma with a complex karyotype (case 19). Two cases demonstrated marked aneuploidy as demonstrated here.

FIGS. 9A-B. Cytogenetic aberrations at 8q13 in Mullerian adenosarcoma. A: Case 16, demonstrating a deletion on the long arm of chromosome 8, involving the 8q13 locus (del(8)(q13q22)). B: Case 14, demonstrating a similar deletion as seen in case 16, but additional insertion of genetic material (of uncertain etiology) at 8q13 (ins(8; ?)(q13; ?), del(8)(q13q22)).

DETAILED DESCRIPTION

Figure 1:
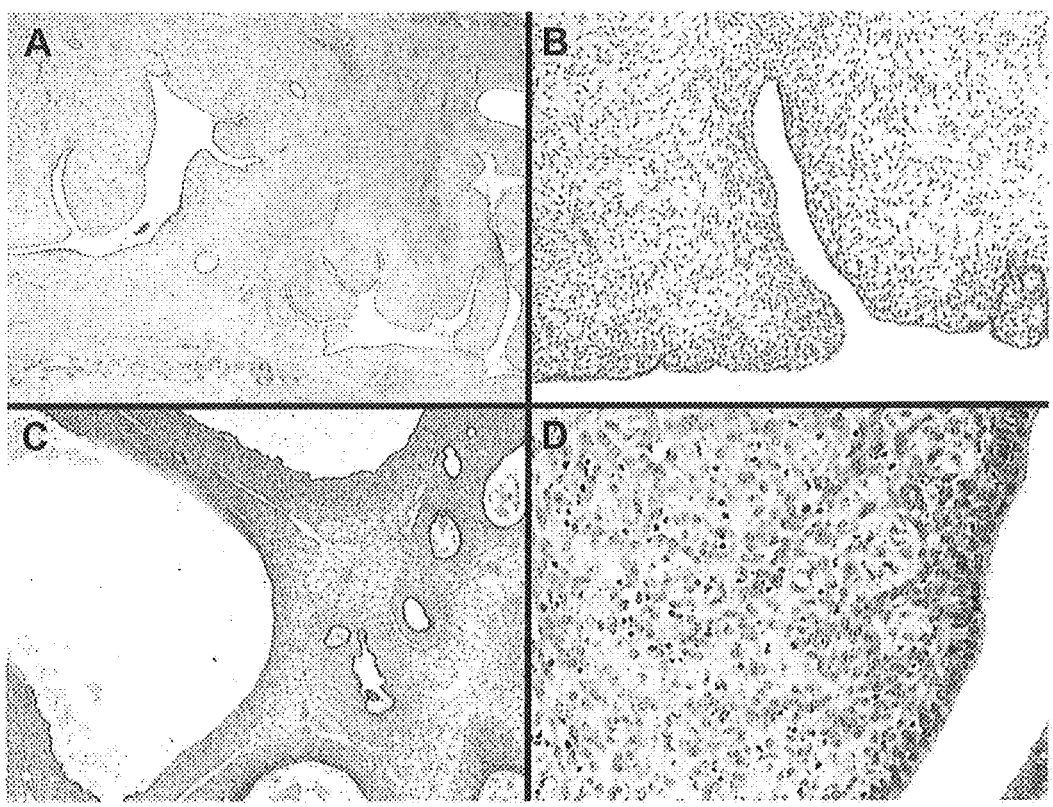
FIGS. 1A-D: Histologic Features of Müllerian Adenosarcoma. A low magnification view of MA demonstrates a phyllodes-like architecture with broad, leaf-like papillae (A; Case #5). On higher power magnification, stromal condensation of the malignant stroma underneath benign epithelium is apparent (B; Case #5). The so-called "rigid cyst" pattern in MA with distinct cuffing of stroma around cystically dilated glands (C; Case #10) was noted in a minority of cases. The tumor cells of MA show subtle cytologic atypia and mitoses next to benign epithelium (D; Case #4).

Müllerian adenosarcoma, first described as such in 1974 by Clement and Scully (1), is an uncommon biphasic malignant tumor of the uterus. Overall, MA is associated with a better prognosis than other uterine sarcomas and carcinosarcomas (25, 26); however, when MA has overgrowth of the sarcomatous component, deep myometrial invasion, or spread beyond the uterus, the survival rate falls to less than 50% (7, 15, 25). When distant metastasis is present, more than 80% of patients die of their disease (15, 27). Although surgery is the mainstay of treatment, adjuvant therapy in the form of chemotherapy, radiation, or both may prolong survival (28) if adverse prognostic features are present. Since the initial description (1), hundreds of uterine and extra-uterine MA have been reported in the literature (2, 3, 6, 11, 12, 29, 30), and although many studies focused on immunohistochemical profiles in attempts to distinguish MA from other uterine tumors and to aid with prognostication (8, 9, 11, 12, 31), no sensitive or specific diagnostic or prognostic marker had been identified before the present invention.

In the present study of 18 MA, we have performed next generation sequencing of a large panel of well-established oncogenes and tumor suppressor genes. The molecular alterations in MA were correlated with the presence or absence of SO, the best histological prognostic parameter. We identified a number of mutations in our series of MA, including known pathogenic mutations as well as novel variants of unclear significance, possibly even germline SNPs.

Mutations and Copy Number Variations in MA

As shown herein, MA with SO is associated with high numbers of CNVs, consistent with acquisition of aneuploidy. This conclusion is supported by previous flow cytometric analysis of MA, which found that all MA with SO were aneuploid but 50% of MA without SO were diploid (15). In the present study, 4 MA had no detectable CNVs. This low rate of aneuploidy further distinguishes them from potentially histologically similar tumors such as carcinosarcoma and leiomyosarcoma.

Figure 6:
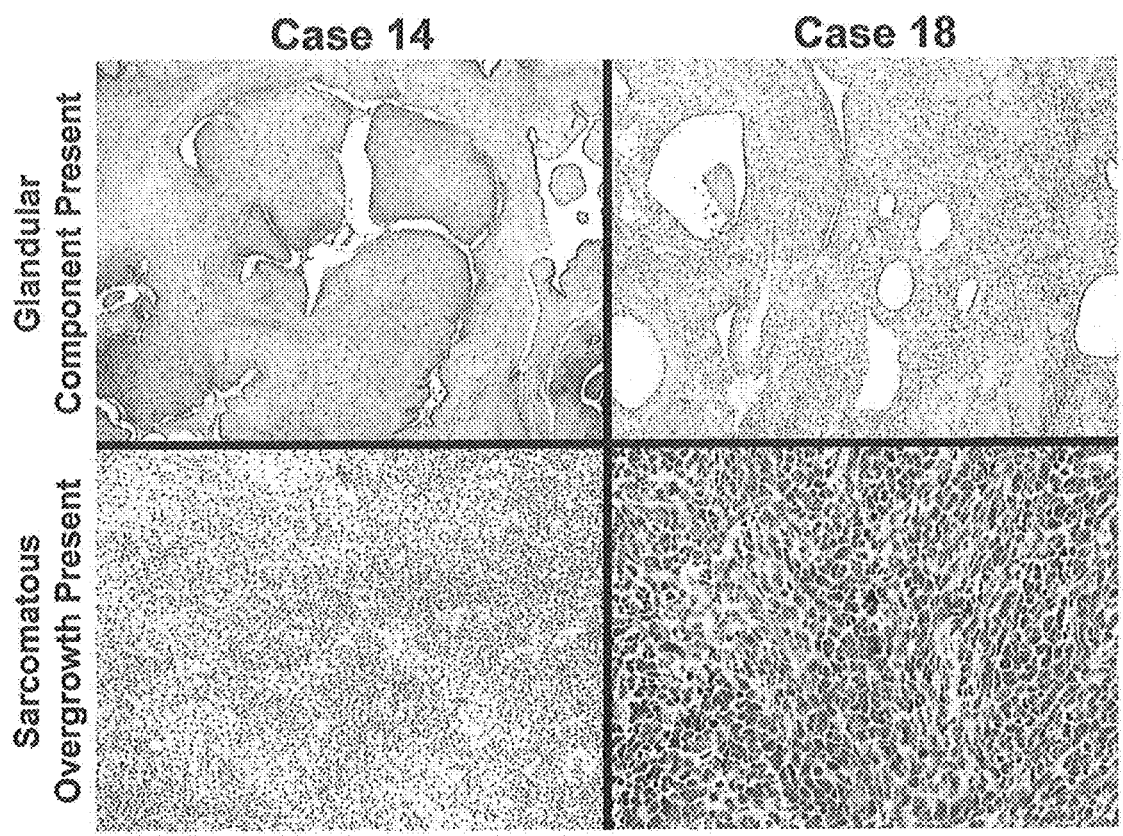
FIG. 6: Independent Sampling of Müllerian Adenosarcomas in Areas With and Without Sarcomatous Overgrowth. In two cases (Case 14, left column; Case 18, right column), core samples were taken from areas of the tumor lacking overt sarcomatous overgrowth (top row) as well as the sarcomatous overgrowth (bottom row).

When considering tumors with SO, there was striking genetic homogeneity between different regions of the same tumor either lacking or manifesting SO (FIG. 6). Areas with SO had only a slightly increased number of CNVs (Table 3) and most missense mutations detected in SO were also present in the corresponding tumor region lacking overt SO (Tables 4 and 5). This suggests that MA with SO accumulate many, if not most, of the genetic changes relatively early in their natural history, which has both diagnostic and prognostic implications.

TP53 mutations are common in sarcomas of the female reproductive tract, particularly uterine carcinosarcoma (32-34) and leiomyosarcoma (33-36); however, TP53 mutations are uncommon in MA (11%), and when present are associated with SO and a more aggressive clinical course. In particular, one tumor harboring a TP53 mutation (case 8) metastasized to the lung. Our findings of infrequent TP53 mutation and altered immunohistochemical expression corroborate previous studies which also suggested an association between p53 overexpression and SO (11, 15, 16). Thus, mutations in TP53 can also be used to determine the presence or risk of developing SO in a subject. Reference genomic sequences for TP53 can be found at NG_017013.2 (Range 5001-24149, RefSeqGene); NC_000017.11 (Range 7668402-7687550, Reference GRCh38.p2 Primary Assembly).

ATRX (α thalassemia/mental retardation syndrome X-linked, located on Xq21.1) encodes a chromatin remodeling protein thought to be important in regulating DNA methylation and telomere stability. Mutations in ATRX are common in various gliomas (37, 38) and pancreatic neuroendocrine tumors (23, 39). The effect of ATRX mutation on prognosis is variable; several studies found an enhanced survival with ATRX mutation in some tumor types (39) but others report a worse prognosis (23, 24). In our study, ATRX mutations were identified in 3 MA; however, only one case showed loss of ATRX expression by IHC. It remains to be determined in future studies whether these different outcomes reflect a common pathobiological mechanism, such as loss of function either by protein instability or inactivation. The presence of ATRX mutations in half of MA with SO (including one case with distant metastasis), but its absence in MA without SO suggests that this may be an indicator of poor prognosis for MA. Thus, mutations in ATRX can also be used to determine the presence or risk of developing SO in a subject. Reference genomic sequences for ATRX can be found at NG_008838.2 (Range 4953-286344, RefSeqGene), and NC_000023.11 (Range 77504878-77786269, Reference GRCh38.p2 Primary Assembly).

MYBL1, located on 8q, was amplified in 50% of MA with SO (cases 8, 15, and 17), but just one without SO (case 12). MYBL1 is a transcription factor involved in cell proliferation, particularly in spermatogenesis, neurogenic and B-lymphoid cell development. MYBL1 is amplified in 10% of uterine carcinosarcoma and 23% of metastatic prostatic adenocarcinoma (Gao et al., Sci. Signal. 6(269):p11 (2013); Cerami et al., Cancer Discovery, 2:401 (2012)), and is commonly either duplicated, truncated, or part of larger chromosomal arm-level gains in diffuse astrocytoma (40). While no tumor-defining cytogenetic arrangement has been discovered in MA, one reported karyotype from a MA with SO included a trisomy of chromosome 8 (41). We have also observed trisomy 8 in 4/7 (57%) MA with SO. Consequently, copy number gains of MYBL1 may be a strong candidate for a recurrent driving event in the progression of MA to sarcomatous overgrowth, and can be used to determine the presence or risk of developing SO in a subject. Reference genomic sequences for MYBL1 are at NC_000008.11 (Range 66562175-66613249, Reference GRCh38.p2 Primary Assembly) and NC_018919.2 (Range 67529290-67580347, Alternate CHM1_1.1).

Low level copy number gains of MDM2 and CDK4 by CNV analysis were identified in 28% of our MA series, accompanied by immunohistochemical expression of MDM2 and CDK4 in the cases with CNV gains. CDK4 and MDM2 protein expression was always focal or diffusely weak in MA, in contrast to the typically strong and diffuse staining pattern seen in well-differentiated and de-differentiated liposarcoma with high-level MDM2 and CDK4 amplification (42, 43). We note that two cases of MA have been reported to express MDM2 by immunohistochemistry (15) (one with and one without SO), corroborating our findings. Recently, it has been recognized that rare cases of endometrial stromal sarcoma can also have MDM2 amplification (unpublished data). HMGA2, a gene located on 12q14.3, between MDM2 and CDK4 (FIG. 5) was not included in the targeted sequencing assay, but given its proximity to MDM2 and CDK4, we tested the immunohistochemical expression of HMGA2. Interestingly, HMGA2 expression was strong and diffuse in nearly all (4/5) cases with CNV gains of the 12g14-15 chromosomal region containing CDK4 and MDM2. Thus, CNV gains of CDK4 and MDM2 can also be used to determine the presence or risk of developing SO in a subject. Reference genomic sequences for MDM2 are at NG_016708.1 (Range 4982-42354, RefSeqGene); NC_000012.12 (Range 68808168-68845544, Reference GRCh38.p2 Primary Assembly); and NC_018923.2 (Range 69170604-69207918, Alternate CHM1_1.1). Reference genomic sequences for CDK4 are at NG_007484.2 (Range 4935-9655, RefSeqGene); NC_000012.12 (Range 57747727-57752447, Reference GRCh38.p2 Primary Assembly), and NC_018923.2 (Range 58109315-58114035, Alternate CHM1_1.1).

The HMGA2 (high-mobility group AT-hook 2) gene encodes a non-histone chromatin-associated high mobility group (HMG) protein. It is not thought to directly regulate gene transcription, but HMGA2 is able to bind to DNA and affect the architectural configuration of chromatin, indirectly allowing for or preventing regulatory complexes access to their DNA binding domains. Although the closely related family member HMGA1 is more commonly implicated in endometrial polyps, HMGA2 has also been implicated in translocations in endometrial polyps (44-51), as well as leiomyoma (44, 52), aggressive angiomyxoma (52, 53), mass-forming endometriosis (54), pulmonary chondroid hamartoma (44, 55), and lipoma (44, 56). In addition, HMGA2 was amplified in at least one benign endometrial polyp, providing an alternate explanation for aberrantly expressing HMGA2 (57). Interestingly, a transgenic mouse model expressing HMGA1 specifically in the uterus produced tumors bearing a striking histologic resemblance to MA in all mice by nine months of age (58). The HMGA2 gene is in the amplicon between MDM2 and CDK4, and its increase was verified by immunohistochemistry as shown herein. There are potential therapeutic implications of our finding of HMGA2 overexpression in a subset of MA, as a breast cancer cell line with high level expression of HMGA2 has been shown to be highly sensitive to the topoisomerase II inhibitor doxorubicin (59); thus doxorubicin can be selected in some embodiments for those subjects with HMGA2 copy number gains. Reference genomic sequences for HMGA2 are at NG_016296.1 (Range 5001-146832, RefSeqGene), NC_000012.12 (Range 65824460-65966291, Reference GRCh38.p2 Primary Assembly), and NC_018923.2 (Range 66185507-66327350, Alternate CHM1_1.1).

In summary, MA, unlike other mullerian tumors, do not commonly harbor TP53 mutations, and frequently have low-level amplification of MDM2 and CDK4. ATRX and TP53 mutations were identified only in cases with SO, and may be prognostically useful. MYBL1 amplification is more common in MA with SO, and may represent segmental genomic amplification or chromosomal arm-level copy gains.

Cytogenetic Abnormalities in Müllerian Adenosarcoma

MA grows slowly in culture and thus karyotypes are difficult to obtain. In our study, successful karyotype was obtained in 67%, with an abnormal karyotype in 64% of these. One might hypothesize that lower grade tumors (those lacking sarcomatous overgrowth) might be more difficult to culture than tumors with sarcomatous overgrowth or metastatic MA composed entirely of sarcoma. In fact, this does not appear to be the case in this series, as primary MA with and without SO and metastatic MA were all evenly distributed between the unsuccessful karyotype, normal karyotype, and abnormal karyotype categories. However, our study supports the conclusion that MAs lacking sarcomatous overgrowth do not have markedly complex karyotypes.

Five of seven cases with abnormal but non-complex karyotypes showed alterations of chromosome 8, including both extra copies as well as rearrangements. Molecular genetic aberrations in MA are described herein, including amplification of MYBL1, which is located on 8q13. Interestingly, this locus was involved in rearrangements in 2 of the cases in this study. The MYB family of proto-oncogenes are transcription factors involved in regulating cell cycle progression and include the genes MYB, MYBL1 and MYBL2. MYB (located on 6q23.3) is a known oncogene in acute leukemias (Clappier et al. 2007) and adenoid cystic carcinoma (Mitani et al. 2010, West et al. 2011). MYBL1 duplication-truncation or rearrangement was identified in a subset of pediatric grade II astrocytomas (Ramkissoon et al. 2013, Zhang et al. 2013) leading to overexpression of MYBL1 fusion transcripts and loss of critical regulatory domains leading to uncontrolled cell growth (Ramkissoon et al. 2013).

Five cases revealed a normal karyotype. Interestingly, two of these samples were obtained from the same subject; a primary uterine adenosarcoma with sarcomatous overgrowth and a subsequent lung metastasis (Cases 9 and 10). Given the histologic appearance of this tumor (FIG. 1C), a spindle cell sarcoma, the possibility that the karyotype was obtained from cultured non-neoplastic cells cannot be excluded, and in fact is in our opinion favored given the high number of copy number variations including whole arm gains and losses, as inferred via next generation sequencing of MA with sarcomatous overgrowth as shown herein.

The one previously published karyotype of MA by conventional G banding was reported as 47-49, XX, +8, +8, add(10)(q24), add(13)(q34), +19, −21); however, upon further examination using an OctoChrome device and fluorescence in situ hybridization (FISH), the karyotype was further refined to 47-49, XX, +8, +8, del(10) (q24.1q26.1),der(13)t(2; 13)(q21;q34), +19, −21[cp20].ish del(10)(wcp10+), der(13)t(2; 13)(wcp2+,wcp13+) (Chen et al. 2004). It is important to note that this reported case is unusual in that it was an extra-uterine mass in a young (15 year old) girl, without any recognizable low grade MA present. The only overlapping karyotypic aberration with our series of MA is tetrasomy of chromosome 8.

Importantly, none of the rearrangements reported in MA involve the HMGA1 (6p21) or HMGA2 (12q15) loci, which are frequently rearranged in mass-forming endometriosis (Medeiros et al. 2010) and other low grade mesenchymal neoplasms, including endometrial polyps (Medeiros et al. 2007). One study has shown frequent copy number gains at the region of HMGA2 locus, with accompanying increased protein expression as detected by immunohistochemistry in MA. As no aberrations were identified involving the long arm of chromosome 12 in this study by conventional cytogenetics suggests that any alterations at that locus might be too small to detect by conventional G banding karyotype. Endometrial stromal sarcoma (ESS) is sometimes considered in the differential diagnosis with MA. In contrast to ESS, which frequently harbor recurrent translocations associated with gene fusions such as t(7; 17)/JAZF1-SUZ12, t(6; 17)/PHF1-JAZF1, t(1; 6)/MEAF6-PHF1, t(10; 17) (FAM22A/B-YWHAE, t(X; 22)(/BCORZC3H7 and t(X; 17)/MBTD1-CXorf67 (Chiang and Oliva 2011, Dewaele et al 2014), none of these chromosomes were involved in rearrangements in the MAs included in this study, suggesting there might be little overlap in the cytogenetics of these tumors. Of note, trisomy 8 has been reported in ESS (Laxman et al. 1993), and can also be seen in a number of other tumors, suggesting it is not a unique aberration to MA.

In conclusion, we have reported the largest series of karyotypic abnormalities in mullerian adenosarcoma, with only one previously reported karyotype of this uncommon tumor in the literature to date. An abnormal karyotype was identified at our institution in at least 64% of MA. These aberrations do not significantly overlap with the recurrent karyotypic abnormalities reported in ESS or mass-forming endometriosis, entities commonly considered in the differential diagnosis and therefore this difference may be useful in diagnostically challenging cases. High grade sarcomas often have extraordinarily complex cytogenetic aberrations, many of which are not clonal.

Methods of Diagnosing MA and Determining Risk of Developing SO

Included herein are methods for diagnosing MA, and for determining a prognosis. The methods include obtaining a sample containing cells from a subject, evaluating the presence of a mutation or copy number as described herein in the sample (e.g., a CNV in a MYBL1, MDM2, HMGA2, and/or CDK4 gene, and/or a mutation in a TP53 and/or ATRX gene), and comparing the presence and/or copy number with one or more references, e.g., a control reference that represents a sequence or copy number in a normal or non-cancerous cell, e.g., a level in a cell from a uterine polyp, or that represents a sequence or copy number in a benign MA cell, or a disease reference that represents a sequence or copy number in a cell from a tumor that has or is likely to proceed to SO, e.g., a malignant cell. In the present methods, a CNV associated with the presence or risk of MA or MA with SO is a duplication or increase in copy number in a MYBL1, MDM2, HMGA2, and/or CDK4 gene. A mutation in TP53 and/or ATRX gene associated with the presence or risk of MA or MA with SO is a sequence that is different from the reference sequence (e.g., as provided herein) at one or more positions. In some embodiments, the mutation is a mutation shown in Tables 2A-2B, or a mutation known in the art to be associated with oncogenesis.

The presence and/or level (copy number) of a nucleic acid (e.g., a CNV in a MYBL1, MDM2, HMGA2, and/or CDK4 gene, and/or a mutation in a TP53 and/or ATRX gene) can be evaluated using methods known in the art, e.g., using polymerase chain reaction (PCR), reverse transcriptase polymerase chain reaction (RT-PCR), quantitative or semi-quantitative real-time RT-PCR, digital PCR i.e. BEAMing ((Beads, Emulsion, Amplification, Magnetics), Diehl (2006) Nat Methods 3:551-559); RNAse protection assay; Northern blot; various types of nucleic acid sequencing (Sanger, pyrosequencing, NextGeneration Sequencing); fluorescent in-situ hybridization (FISH); or gene array/chips); multiplexed gene expression analysis methods, e.g., RT-PCR, RNA-sequencing, and oligo hybridization assays including RNA expression microarrays; hybridization based digital barcode quantification assays such as the nCounter® System (NanoString Technologies, Inc., Seattle, Wash.; Kulkarni, Curr Protoc Mol Biol. 2011 April; Chapter 25:Unit25B.10) and lysate based hybridization assays utilizing branched DNA signal amplification such as the QuantiGene 2.0 Single Plex and Multiplex Assays (Affymetrix, Inc., Santa Clara, Calif.; see, e.g., Linton et a., J Mol Diagn. 2012 May-June; 14(3):223-32); SAGE, high-throughput sequencing, multiplex PCR, MLPA, luminex/XMAP, or branched DNA analysis methods. As used herein, a "test sample" refers to a biological sample obtained from a subject of interest including a cell or cells, e.g., tissue, from the tumor. (Lehninger Biochemistry (Worth Publishers, Inc., current addition; Sambrook, et al, Molecular Cloning: A Laboratory Manual (3. Sup.rd Edition, 2001); Bernard (2002) Clin Chem 48(8): 1178-1185; Miranda (2010) Kidney International 78:191-199; Bianchi (2011) EMBO Mol Med 3:495-503; Taylor (2013) Front. Genet. 4:142; Yang (2014) PLOS One 9(11): e110641); Nordstrom (2000) Biotechnol. Appl. Biochem. 31(2):107-112; Ahmadian (2000) Anal Biochem 280:103-110. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of a nucleic acid (e.g., a CNV in a MYBL1, MDM2, HMGA2, and/or CDK4 gene, and/or a mutation in a TP53 and/or ATRX gene). Measurement of the level of a marker described can be direct or indirect. For example, the copy number of MYBL1, MDM2, HMGA2, and/or CDK4 can be directly quantitated. Alternatively, the amount of a biomarker can be determined indirectly by measuring abundance levels of cDNA, amplified RNAs or DNAs, or by measuring quantities or activities of mRNAs or proteins, or other molecules that are indicative of the expression level of the biomarker. In some embodiments a technique suitable for the detection of alterations in the structure or sequence of nucleic acids, such as the presence of deletions, amplifications, or substitutions, can be used for the detection of biomarkers of this invention.

RT-PCR can be used to detect mutations and CNV. The first step in expression profiling by RT-PCR is the reverse transcription of the RNA template into cDNA, followed by its exponential amplification in a PCR reaction (Ausubel et al (1997) Current Protocols of Molecular Biology, John Wiley and Sons). To minimize errors and the effects of sample-to-sample variation, RT-PCR is usually performed using an internal standard, which is expressed at constant level among tissues, and is unaffected by the experimental treatment. Housekeeping genes as known in the art are most commonly used.

Gene arrays are prepared by selecting probes which comprise a polynucleotide sequence, and then immobilizing such probes to a solid support or surface. For example, the probes may comprise DNA sequences, RNA sequences, co-polymer sequences of DNA and RNA, DNA and/or RNA analogues, or combinations thereof. The probe sequences can be synthesized either enzymatically in vivo, enzymatically in vitro (e.g. by PCR), or non-enzymatically in vitro.

In some embodiments, the methods can include detecting protein levels of MYBL1, MDM2, HMGA2, and/or CDK4, and comparing the protein levels to reference protein levels in a normal cell. A duplication or increase in copy number is expected to result in an increase in protein expression levels, so an increase in protein expression levels over a reference or threshold level can be used as a proxy for CNV. The presence and/or level of a protein can be evaluated using methods known in the art, e.g., using standard electrophoretic and quantitative immunoassay methods for proteins, including but not limited to, Western blot; enzyme linked immunosorbent assay (ELISA); biotin/avidin type assays; protein array detection; radio-immunoassay; immunohistochemistry (IHC); immune-precipitation assay; FACS (fluorescent activated cell sorting); mass spectrometry (Kim (2010) Am J Clin Pathol 134:157-162; Yasun (2012) Anal Chem 84(14):6008-6015; Brody (2010) Expert Rev Mol Diagn 10(8):1013-1022; Philips (2014) PLOS One 9(3): e90226; Pfaffe (2011) Clin Chem 57(5): 675-687). The methods typically include revealing labels such as fluorescent, chemiluminescent, radioactive, and enzymatic or dye molecules that provide a signal either directly or indirectly. As used herein, the term "label" refers to the coupling (i.e. physically linkage) of a detectable substance, such as a radioactive agent or fluorophore (e.g. phycoerythrin (PE) or indocyanine (Cy5), to an antibody or probe, as well as indirect labeling of the probe or antibody (e.g. horseradish peroxidase, HRP) by reactivity with a detectable substance.

In some embodiments, an ELISA method may be used, wherein the wells of a mictrotiter plate are coated with an antibody against which the protein is to be tested. The sample containing or suspected of containing the biological marker is then applied to the wells. After a sufficient amount of time, during which antibody-antigen complexes would have formed, the plate is washed to remove any unbound moieties, and a detectably labelled molecule is added. Again, after a sufficient period of incubation, the plate is washed to remove any excess, unbound molecules, and the presence of the labeled molecule is determined using methods known in the art. Variations of the ELISA method, such as the competitive ELISA or competition assay, and sandwich ELISA, may also be used, as these are well-known to those skilled in the art.

In some embodiments, an IHC method may be used. IHC provides a method of detecting a biological marker in situ. The presence and exact cellular location of the biological marker can be detected. Typically a sample is fixed with formalin or paraformaldehyde, embedded in paraffin, and cut into sections for staining and subsequent inspection by light microscopy. Current methods of IHC use either direct or indirect labelling. The sample may also be inspected by fluorescent microscopy when immunofluorescence (IF) is performed, as a variation to IHC.

Mass spectrometry, and particularly matrix-assisted laser desorption/ionization mass spectrometry (MALDI-MS) and surface-enhanced laser desorption/ionization mass spectrometry (SELDI-MS), is useful for the detection of biomarkers of this invention. (See U.S. Pat. Nos. 5,118,937; 5,045,694; 5,719,060; 6,225,047).

Antibodies to MYBL1, MDM2, HMGA2, and CDK4 can be generated using standard methods or obtained commercially. Protein sequences for MYBL1, MDM2, HMGA2 and CDK4 are provided below.

| Protein | GenBank Acc. No. |
|---|---|
| MYBL1 | NP_001073885.1 (isoform 1), NP_001138227.1 (isoform 2), NP_001281211.1 (isoform 3) |
| MDM2 | NP_002383.2 (isoform a), NP_001138809.1 (isoform g), NP_001138811.1 (isoform h), NP_001138812.1 (isoform i), NP_001265391.1 (isoform l) |
| CDK4 | NP_000066.1 |
| HMGA2 | NP_003474.1 (isoform a), NP_003475.1 (isoform b), NP_001287847.1 (isoform c), NP_001287848.1 (isoform d) |

In some embodiments, the level (copy number) is considered a threshold level, and the presence of a copy number above the threshold indicates that the subject has a tumor that has or is likely to proceed to SO.

The sample can be, e.g., a biopsy (including a needle biopsy) or a resection specimen (e.g., from a hysterectomy or resection of extra-uterine masses), e.g., any sample that includes cells from a mass known or suspected to be a MA.

The reference or predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

Subjects associated with predetermined values are typically referred to as reference subjects. For example, in some embodiments, a control reference subject does not have does not have MA, or has MA without SO.

A disease reference subject is one who has, or has an increased risk of developing, MA or MA with SO. An increased risk is defined as a risk above the risk of subjects in the general population, e.g., the population of subjects with MA.

Thus, in some cases the presence of a copy number less than a reference level is indicative of a clinical status (e.g., indicative of the absence of MA with SO, e.g., the absence of MA, the absence of MA with SO, or a low risk of developing MA with SO as compared to a subject who has a copy number above the reference level). In some cases the presence of a copy number in a subject that is greater than or equal to the reference level is indicative of the presence of leukemia, e.g., the presence of MA with SO, or an increased risk of developing MA with SO as compared to a subject who has a copy number below the reference level; these subjects might be considered to have a high likelihood of developing the disease within weeks to months, even if at present they do not have full-blown SO (e.g., some, but less than 25%, of the tumor is composed of sarcoma without an epithelial component).

In some embodiments, the subject has had surgery to treat MA, and the presence of a mutation or copy number below a reference level indicates that remission continues or that the subject has a low risk of relapse in the near term (e.g., within the next two weeks, month, six months, year, or two years); in these subjects, the presence of a mutation or copy number above a reference level can indicate that the subject has had or is about to have a relapse, e.g., the subject has a high risk of relapse in the near term (e.g., within the next two weeks, month, six months, year, or two years).

In some embodiments, the amount by which the level in the subject is greater than the reference level is sufficient to distinguish a subject from a control subject, and optionally is statistically significantly greater than the level in a control subject. In cases where the copy number in a subject is "equal to" the reference copy number, the "being equal" refers to being approximately equal (e.g., not statistically different).

The predetermined value can depend upon the particular population of subjects (e.g., human subjects) selected. Appropriate ranges and categories can be selected with no more than routine experimentation by those of ordinary skill in the art.

In characterizing likelihood, or risk, numerous predetermined values can be established.

In some embodiments, as an alternative to or in addition to detecting copy number variations, the methods include detecting the presence of one or more mutations that are associated with the presence of or increased risk of developing MA with SO, as described herein.

Methods of Treatment

In some embodiments, once it has been determined that a person has MA, e.g., MA with SO, or has an increased risk of developing MA, e.g., MA with SO, then a treatment as described herein can be administered.

MA can be present in the uterine corpus, cervix, vagina, fallopian tubes, ovaries, and peritoneum, as well as rarely outside the female genital tract. The typical symptoms associated with MA are abnormal uterine bleeding, vague pain in the lower abdomen, cervical neoplasms, and enlargement of the uterus to varying degrees. Pain, foul smelling vaginal discharge, or symptoms of pelvic pressure have also been reported. Adenosarcomas are typically polypoid masses that can be soft or firm and range from 1 to 17 cm, with an average maximum dimension of about 5 cm. Multiple papillary or polypoid masses are sometimes seen. The cut surface of the mass is tan, brown, or gray with microcystic architecture, sometimes with areas of hemorrhage and necrosis.

A diagnosis of MA can be made, e.g., using methods described herein (e.g., based on the presence of a tumor or mass with a mutation in the ATRX gene, and/or a CNV in a MYBL1, MDM2, HMGA2 and/or CDK4 gene) or methods known in the art, e.g., based on detection of morphologic features by routine hematoxylin and eosin examination. Morphologic features considered diagnostic parameters or at least suggestive of MA include phyllodes-like architecture (a frondlike growth pattern: thin papillae or broad polypoid fronds that project into glands or from the surface of tumor), intraglandular polypoid projections, rigid cysts, periglandular stromal cuffing, subepithelial condensation, stromal cytologic atypia, and mitotic activity (maximum per 10 high-power fields (HPF)). The appearance of the periglandular stromal cuff, when present, can be further assessed as being hypercellular, hypocellular, or loose/edematous and as having either a well-demarcated or indistinct border. See, e.g., (Shi et al., Aust N Z Obstet Gynaecol. 48 (6): 596-600 (2008); Howitt et al., Am J Surg Pathol 39(1):116-26 (2015); Blom et al. Int J Gynecol Cancer. January 1999; 9(1):37-43; Clement et al. Hum Pathol. April 1990; 21(4):363-81; Kaku et al. Int J Gynecol Pathol. 1992; 11(2):75-88). Once a subject has been identified as having (or being at increased risk of developing) MA, e.g., MA with SO, then a treatment as known in the art or described herein can be administered.

The stage of disease in the subject is presently determined using the FIGO staging for uterine sarcomas (Int J Gynecol Obstetrics. 2009; 104:179 (2009)), or the TNM staging for adenosarcomas (Edge et al., (Eds) AJCC Cancer Staging Manual, 7th Ed. Springer:New York; 2010:488 (2010)). The FIGO stages are as follows:

| Stage I | Tumor limited to uterus |
|---|---|
| | IA Tumor limited to endometrium/endocervix with no myometrial invasion |
| | IB Less than or equal to half myometrial invasion |
| | IC More than half myometrial invasion |
| II | Tumor extends beyond the uterus, within the pelvis |
| | IIA Adnexal involvement |
| | IIB Tumor extends to extrauterine pelvic tissue |
| III | Tumor invades abdominal tissues (not just protruding into the abdomen) |
| | IIIA One site |
| | IIIB More than one site |
| | IIIC Metastasis to pelvic and/or para-aortic lymph nodes |

-continued

| Stage I | Tumor limited to uterus |
|---|---|
| IV | |
| | IVA Tumor invades bladder and/or rectum |
| | IVB Distant metastasis |

See, e.g., D'Angelo and Prat, Gynecol Oncol. 2010 Jan; 116(1): 131-9.

Surgical resection is the typical treatment for Mullerian adenosarcoma. The extent of surgery is based on surgical pathological staging criteria, e.g., using the (Shi Y et al., Aust N Z Obstet Gynaecol. 48 (6): 596-600 (2008)). For stage I patients, a total hysterectomy, or modified radical hysterectomy are commonly performed. Laparotomy, surgical excision of the neoplasm, pelvic lymphadenectomy may also be performed. Stage III patients may receive modified radical hysterectomy, bilateral adnexectomy, or omentectomy. Beyond surgery there is no consensus on guiding adjuvant therapy. Certain patients may receive pre- or postoperative chemotherapy (three to six courses) consisting of doxorubicin and carboplatin, cyclophosphamide, vincristine and carboplatin, or dacarbazine. The decision to administer posteroperative chemotherapy may be based on deeper myometrial invasion (Tackin et al., 2006) and in the context of sarcomatous overgrowth. Dependent on the estrogen (ER) and progesterone (PR) receptors status of the tumor, endocrine therapy may be administered (for example, treatments with anti-estrogens such as pure estrogen receptor antagonisists (e.g., fulvestrant) or aromatase inhibitors for ER+ tumors, anti-progestins such as telapristone for PR+ tumors, as well as medically or surgically inducing menopause by administering GnRH agonists like leuprolide or oophorectomy; an aromatase inhibitor can be used in a subject with an ER and/or PR positive tumor). Thus, the methods can include determining the ER and/or PR status of the tumor, using methods known in the art, e.g., using immunohistochemistry; see, e.g., Hammond et al., Journal of Clinical Oncology, Vol 28, Issue 16 (June), 2010: 2784-2795, and optionally selecting a treatment for the subject that includes a treatment described above based on the PR and/or ER status of the tumor.

In some of the present methods, the treatment can be selected based on the presence of a tumor or mass with a mutation in the ATRX gene, and/or a CNV in a MYBL1, MDM2, HMGA2, and/or CDK4 gene. The methods can include selecting or administering an aggressive treatment, e.g., a treatment typically reserved for a high stage patient, to subjects who have a tumor or mass with a mutation in an ATRX gene, and/or a CNV in a MYBL1, MDM2, HMGA2, and/or CDK4 gene. For example, the methods can include a radical hysterectomy (complete removal of the uterus, cervix, upper vagina, and parametrium, a wide area of ligaments and tissues around these organs, as well as optionally ovaries, fallopian tubes, or nearby lymph nodes) or modified radical hysterectomy (to remove the uterus, cervix, upper part of the vagina, ligaments and tissues that closely surround these organs, and optionally nearby lymph nodes). In these methods, the subject may have only an atypical polyp (e.g., not diagnosable with MA, e.g., lacking one or more diagnostic features of MA), or may have MA without SO. The aggressive treatment can also include administration of chemotherapy, e.g., pre- or postoperative chemotherapy (three to six courses), e.g., including doxorubicin and carboplatin, cyclophosphamide, vincristine and carboplatin, or dacarbazine. In some instances, pelvic radiation therapy may be administered, especially for local control.

MYBL1 Inhibitors

In some embodiments, the methods described herein can include selecting or administering an MYBL1 inhibitor to a subject who has copy number gains in MYBL1. An exemplary MYBL1 inhibitor is mexicanin-I ((3as,4r,4ar,7ar,8r, 9as)-4-hydroxy-4a,8-dimethyl-3-methylidene-3,3a,4,4a,7a, 8,9,9a-octahydroazuleno[6,5-b]furan-2,5-dione), a sesquiterpene lactone isolated from the flowering plant *Helenium mexicanum*. See, Bujnicki et al., Leukemia 2011; 26: 615-702. Thus, the methods described herein include the use of pharmaceutical compositions comprising a MYBL1 inhibitor, e.g., mexicanin I, as an active ingredient. Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) for vaginal or rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser, optionally with instructions for administration, for use in a method described herein.

EXAMPLES

The invention is further described in the following examples, which do not limit the scope of the invention described in the claims.

Materials and Methods

The following materials and methods were used in the examples set forth herein.

Case Selection

We obtained 20 MA samples from 18 subjects, including 12 cases without SO and 6 with SO, diagnosed between 1997 and 2013, with approval from the Institutional Review Board. The H&E slides for all cases were reviewed by three gynecologic pathologists and the diagnosis of MA was confirmed using standard diagnostic criteria (1, 2, 4) by consensus review at a multi-headed microscope. For all cases, H&E slides with the tumor circled were matched to the corresponding formalin fixed paraffin embedded (FFPE) tumor block, which was then cored (using a core punch device to generate 5-10 one millimeter core punch samples). Two MA cases with SO had independent sampling and testing of both areas of tumor with and without SO. Of the remaining 4 MA cases associated with SO, the area of SO was sampled in 3 cases, and typical biphasic histology was sampled in one tumor.

Targeted Genomic Sequencing Assay

FFPE samples were digested in proteinase K overnight, and DNA was isolated according to the manufacturer's protocol (QIAamp DNA Mini Kit, QIAGEN, Gaithersburg, Md.). DNA concentration was assessed using PicoGreen ds DNA detection (Life Technologies, Carlsbad, Calif.). All cases with at least 50 ng of DNA (up to 200 ng) were subjected to next generation sequencing (NGS) of the complete exons of 275 oncogenes and tumor suppressor genes. Ninety-one intronic regions across 30 genes were also included for the evaluation of structural rearrangements. Targeted sequences were captured using a solution-phase Agilent SureSelect hybrid capture kit (Agilent Technologies, Inc., Santa Clara, Calif.), and massively parallel sequencing was performed on an Illumina HiSeq 2500 sequencer (Illumina, Inc., San Diego, Calif.). Mutation calls were made using Mutect (17) and GATK software (18-20) (Broad Institute, Cambridge, Mass.) and gene level copy number alterations at the level of individual genes were assessed using VisCap Cancer (Dana Farber Cancer Institute, Boston, Mass.). The sequence reads were aligned and processed through a bioinformatics pipeline to identify single nucleotide variations (SNVs) including small indels, and any alteration reported at a frequency of >1% in the general population (based on the Exome Variant Server; evs.gs.washington.edu/EVS/, data release ESP6500SI-V2) was classified as a single nucleotide polymorphism (SNP) and subsequently filtered out from further consideration. Of note, the majority of SNPs occur at a frequency of <1%, so some fraction of the called variants might represent germline events. This NGS assay is a CLIA-approved test at our institution for SNV detection in other tumor types (e.g., lung) that, for clinical purposes, does not need any additional validation studies. Garcia et at has demonstrated 98.8% precision of our NGS assay using orthogonal methods (21). Moreover, Spencer et at also found >98% accuracy of hybrid capture NGS when compared to orthogonal platforms (22). For these reasons, additional independent sequencing validation studies were not pursued. Gene level copy number variations (CNVs) were quantified as a ratio of fractional coverage of each exon in the tumor sample normalized against the fractional coverage of the corresponding exon in a panel of normal samples. Circular binary segmentation was then employed to assemble exons into contiguous multi-exon regions. The copy number data for each segment were then displayed visually and interpreted manually by a certified Molecular Pathologist.

Immunohistochemistry

The Envision Plus detection system (Dako, Carpinteria, Calif.) was used for all antibodies. The following antibodies and dilutions were used: 1) p53 mouse monoclonal antibody (Immunotech, clone DO-1) 1:1200, 2) MDM2 mouse monoclonal antibody (EMD, clone IF2) 1:20, 3) CDK4 mouse monoclonal antibody (Invitrogen, clone DCS-31) 1:150, 4) HMGA2-P1 rabbit polyclonal antibody (BioCheck, Inc, catalog #59170AP) 1:1000, 5) MYBL1 rabbit polyclonal antibody (Sigma, catalog #HPA008791) 1:400, and 6) ATRX rabbit polyclonal antibody (Sigma, catalog #HPA001906) 1:100. The antigen retrieval method for all stains included heat induced epitope retrieval in 10 mM Citrate Buffer, pH 6.0 with a pressure cooker. Appropriate positive and negative controls were used throughout. Nuclear staining was considered positive for all immunohistochemical stains, and semi-quantitative analysis was performed as follows: intensity was scored as strong (3+), moderate (2+), weak (1+), or negative (0), and distribution of staining was scored as diffuse (>75%), moderate (25-75%), focal (<25%), or negative (0%).

Fluorescence In Situ Hybridization (FISH)

Two cases were selected for MDM2 FISH (cases 10 and 14), which was performed on 5 micron FFPE tissue sections. Probes for MDM2 at 12q14.3-q15 and D12Z1 (chromosome 12 alpha-satellite probe) at 12p11.1-q11.1 (Cytocell, Ltd) and nuclei were co-denatured simultaneously, followed by hybridization and washing. 50 nuclei were counted in each case and the ratio of MDM2 copies to centromeric probe signals were used to determine amplification status.

Statistical Analysis

T-tests were performed to determine significance of the difference in numbers of mutation and copy number variations between MA with and without SO.

Cytogenetic Analysis

All cases of MA with fresh tissue submitted for cytogenetic analysis (n=21) at Brigham and Women's Hospital (BWH) were included in this study. Conventional cytogenetic analysis was performed on GTG-banded metaphases obtained after short-term culture using standard protocols in our cytogenetics laboratory. Digital images of all karyotypes obtained were reviewed by a cytogeneticist (P.D.C.) and all reported findings were confirmed. Hematoxylin and eosin (H&E) slides of tumor, when available, were also reviewed by gynecologic pathologists (B.E.H., M.R.N., and B.J.Q.) for confirmation of the diagnosis and evaluation of morphologic features including the presence or absence of SO. This study was approved by the BWH institutional review board.

Example 1

Pathologic and Clinical Features

The clinicopathologic features of subjects included in this study are summarized in Table 1, and representative histologic features of tumors are illustrated in FIG. 1. The mean patient age at diagnosis was 58.6 years (range 21-82 years), and most were treated with hysterectomy (17/18; 94%) or hysterectomy with bilateral salpingo-oophorectomy (15/18; 83%). Ten patients also had sampling of omentum, lymph nodes, or both. The mean tumor size (as measured in the hysterectomy specimen) was 6.3 cm (range 2 cm-12 cm); however, multiple cases with tumor size less than 4 cm were preceded by a dilation and curettage, which may have resulted in underestimation of tumor size. Myoinvasion was present in 8/17 (47%), with 4 showing invasion of less than 50% of the myometrial thickness, 1 with approximately 50% myoinvasion, and 3 with greater than 50% myoinvasion. In two cases (cases 2 and 7), endometriosis was also diagnosed. Five (27%) recurred (4 with SO; 1 without SO) including both locoregional (n=4) and distant metastatic sites (n=2). The one case without SO that recurred (case 7) was associated with endometriosis, and thus potentially could represent multicentric primary disease or independent extra-uterine primaries. Three subjects with recurrence subsequently received chemotherapy and 2 underwent radiation brachytherapy to the vaginal cuff, which in one case was accompanied by pelvic radiation therapy. The mean follow-up time was 72.6 months (range 0.5-207 months); all patients were alive at the time of last followup. Four (22%; all with SO) were alive with known persistent or recurrent disease, and 14 (78%) were alive without evidence of disease.

TABLE 1

Clinicopathologic Characteristics of Müllerian Adenosarcoma.

| Case # | Tumor Size | SO | Myoinvasion | Age (years) | Surgery | Adjuvant Therapy | Time to recurrence (months) | Site(s) of recurrence | Time to last followup (months) | Status at last followup |
|---|---|---|---|---|---|---|---|---|---|---|
| 1 | ND | (−) | ND | 31 | D&C (×2) | None | N/A | N/A | 43.5 | ANED |
| 2 | 3.2 cm* | (−) | >50% | 26 | TAH, BSO, LNs, Omentum | None | N/A | N/A | 146.7 | ANED |
| 3 | 2 cm* | (−) | <50% | 21 | TAH | None | N/A | N/A | 50.1 | ANED |
| 4 | ND | (−) | Absent | 50 | TAH, BSO, LNs, Omentum | None | N/A | N/A | 187.1 | ANED |
| 5 | 7.5 cm | (−) | Absent | 75 | TAH, BSO | None | N/A | N/A | 0.5 | ANED |
| 6 | 6 cm | (−) | 50% | 61 | TAH, BSO | None | N/A | N/A | 37.7 | ANED |
| 7 | 2.7 cm‡ | (−) | Absent | 56 | TAH, BSO | Chemotherapy after recurrence | 3.5 months | Vagina, Pelvis | 39.9 | ANED |
| 9 | 10 cm | (−) | Absent | 82 | TAH, BSO | None | N/A | N/A | 23.8 | ANED |
| 10 | 5.5 cm | (−) | Absent | 68 | TAH, BSO, LNs | None | N/A | N/A | 207 | ANED |
| 11 | 11 cm | (−) | Absent | 77 | TAH, BSO, LNs, Omentum | Brachy XRT to vaginal cuff | N/A | N/A | 14.7 | ANED |
| 12 | 3.5 cm* | (−) | Absent | 50 | TAH, BSO, LNs, Omentum | None | N/A | N/A | 118.7 | ANED |
| 13 | 2.5 cm | (−) | Absent | 39 | TAH | None | N/A | N/A | 142.7 | ANED |
| 8 | 8.2 cm | (+) | <50% | 66 | TAH, BSO, LNs, Omentum | Chemotherapy | 2 months | Abdomen | 53.7 | AWD |
| 14 | 7 cm | (+) | Absent | 72 | TAH, BSO, LNs, Omentum | None | N/A | N/A | 181.5 | ANED |
| 15 | 7.5 cm | (+) | <50% | 65 | TAH, BSO, LNs, Omentum | Pelvic & brachy XRT | N/A | N/A | 34 | ANED |
| 16 | 12 cm | (+) | >50% | 71 | TAH, BSO, LNs, Omentum | None | 1.5 months | Lung | 5 | AWD |
| 17 | 10 cm | (+) | >50% | 72 | TAH, BSO | None | 9.5 months | Pelvis | 10 | AWD |
| 18 | 2.5 cm* | (+) | <50% | 60 | TAH, BSO, Omentum | Chemotherapy after recurrence | 9.2 months | Abdomen, Lung | 10.9 | AWD |

SO: Sarcomatous overgrowth;

ND: No data;

TAH: Total abdominal hysterectomy;

BSO: Bilateral salpingo-oophorectomy;

LN: Lymph node;

XRT: Radiation therapy;

N/A: Not applicable;

ANED: Alive with no evidence of disease;

AWD: Alive with disease.

*Size reported on hysterectomy; previous D&C of tumor performed.

‡ size by report (primary tumor reviewed in consultation; vaginal recurrence resected at BWH and included in this study)

Example 2

Genomic Alterations Overview

The quality standard used for next generation sequencing in our laboratory is 30-fold coverage of target sequences for at least 80% of the interrogated sequences. All of the samples in this study passed this test. A graphic summary of the most common (>2) single nucleotide variations (SNV) and copy number variations (CNV) results across all cases can be seen in Tables 2A and 3A. A complete list of all SNVs and CNVs found in this study is present in Tables 2B and 3B. It is important to note that despite application of a dynamic variant filtration system built into our informatics pipeline to exclude common SNPs and recurrent sequencing artifacts, some of our reported variants may represent rare germline events.

TABLE 2A

Recurrent Mutations in Müllerian Adenosarcoma.

| Gene | Case Numbers | Amino Acid Changes‡ |
|---|---|---|
| AKT1 | 3, 5, 9 | p.D323G, p.E17K, p.E17K |
| ALOX12B | 8, 9 | p.H98fs, p.R19W |
| APC | 11, 14 | p.G998fs, p.N1118D |
| ARID2 | 3, 6, 18 | p.A1569T, p.A1569T, p.T573M |
| ATM | 7, 12, 17 | p.K482Q, p.D1099N, p.D2448Y |
| ATRX | 8, 16, 17 | p.E2063D, p.R1426*, p.R1093M |
| BCOR | 8, 9, 17, 18 | p.N1459S, p.T870S, p.S543*, p.R74H |
| BCORL1 | 1, 9 | p.G533R, p.K1053R |
| CCND1 | 7, 11 | p.D267G, p.N198S |
| CUX1 | 3, 14 | p.V978I, p.L525V |
| DICER1 | 3, 8 | p.D989fs, p.E1705V |
| DMD | 5, 10 | p.E692*, p.R943C |
| EP300 | 9, 16 | p.M289V, p.L2081F |
| ERBB2 | 1, 8, 9 | p.R536Q, p.A1216D, p.R897G |
| ERCC4 | 9, 13 | p.PR194del, p.P379S |
| EXT2 | 11, 17 | p.V120I, p.E530K |
| FANCA | 1, 14 | p.P1175L, p.S858R |
| FANCF | 7, 17 | p.S24G, p.A186V |
| FLT4 | 2, 11 | p.P954S, p.P954S |
| GLI2 | 8, 11, 17 | p.A40V, p.V37M, p.R1008S |
| GLI3 | 4, 18 | p.H1200D, p.I749V |
| GSTM5 | 2, 5 | p.A177V, p.R187C |
| IGF1R | 6, 17 | p.N202S, p.T1366P |
| KDM6A | 5, 9 | p.L872del, p.F141L |
| KDM6B | 1, 12 | p.P906A, p.V968G |
| MLL | 4, 14, 16 | p.V776I, p.L989F, p.E502K |
| MLL2 | 2, 6, 8, 12 | p.P2271S, p.T1246M, p.3860_3861QQ > Q, p.R3099H |
| NFKBIZ | 9, 18 | p.G102A, p.A381V |
| NOTCH2 | 2, 6, 9, 12, 16 | p.A3F, p.L1413H, p.R1800C, p.D1327G, p.G240S |
| PIK3C2B | 4, 14, 18 | p.A577S, p.A577S, p.N232del |
| PRAME | 2, 9, 12 | p.R459S, p.R263C, p.V384I |
| PRKDC | 3, 12, 12, 18 | p.T3869M, p.M2356V, p.A1461T, p.G3936S |
| RARA | 11, 15 | p.T181M, p.P20A |
| RET | 13, 18 | p.S365L, p.S1002N |
| ROS1 | 1, 9, 10 | p.R466Q, p.A974V, p.S653F |
| SDHC | 12, 13 | p.K116R, p.E144Q |
| SF1 | 3, 16 | p.G392A, p.586_586P > PPP |
| SMARCA4 | 4, 8 | p.V1302I, p.Y820* |
| SMO | 4, 13 | p.R173H, p.R400C |
| TET2 | 1, 9 | p.V1718L, p.V1718L |
| TP53 | 16, 18 | p.R249M, p.P219fs |
| TSC2 | 15, 17 | p.A1429S, p.F1510del |

‡Mutations are listed in the same order as the case number.

TABLE 2B

All Mutations Detected in Müllerian Adenosarcoma Sample

| case # | SO? | gene | Mutation | Position | Coverage | A.F. | canonical AA change | Best Effest AA change | type of mutation |
|---|---|---|---|---|---|---|---|---|---|
| 14 | 1 | ABL1 | G/A | 9:133759793 | 14 | 0.5 | p.G706S | p.G725S | missense |
| 3 | 0 | AKT1 | T/C | 14:105239419 | 38 | 0.18 | p.D323G | p.D323G | missense |
| 5 | 0 | AKT1 | C/T | 14:105246551 | 41 | 0.32 | p.E17K | p.E17K | missense |
| 9 | 0 | AKT1 | C/T | 14:105246551 | 31 | 0.16 | p.E17K | p.E17K | missense |
| 8 | 1 | ALOX12B | TG/T | 17:7989393 | 55 | 0.58 | p.H98fs | p.H98fs | frameshift |
| 9 | 0 | ALOX12B | G/A | 17:7990706 | 59 | 0.08 | p.R19W | p.R19W | missense |
| 11 | 0 | APC | TCA/T | 5:112174285 | 178 | 0.19 | p.G998fs | p.G998fs | frameshift |
| 14 | 1 | APC | A/G | 5:112174643 | 103 | 0.49 | p.N1118D | p.N1118D | missense |
| 1 | 0 | AR | C/G | X:66765122 | 65 | 0.66 | p.A45G | p.A45G | missense |
| 8 | 1 | ARID1A | C/G | 1:27101434 | 62 | 0.44 | p.Y1572* | p.Y1572* | nonsense |
| 1 | 0 | ARID1B | A/AGGC | 6:157100116 | 11 | 0.45 | p.293_293G > GG | p.293_293G > GG | indel |
| 3 | 0 | ARID2 | G/A | 12:46246611 | 88 | 0.42 | p.A1569T | p.A1569T | missense |
| 6 | 0 | ARID2 | G/A | 12:46246611 | 90 | 0.43 | p.A1569T | p.A1569T | missense |
| 18 | 1 | ARID2 | C/T | 12:46243365 | 132 | 0.44 | p.T573M | p.T573M | missense |
| 18 | 1 | ASXL1 | G/T | 20:31022443 | 95 | 0.37 | p.G643V | p.G643V | missense |
| 7 | 0 | ATM | A/C | 11:108121636 | 168 | 0.5 | p.K482Q | p.K482Q | missense |
| 12 | 0 | ATM | G/A | 11:108150228 | 64 | 0.55 | p.D1099N | p.D1099N | missense |
| 17 | 1 | ATM | G/T | 11:108200975 | 192 | 0.24 | p.D2448Y | p.D2448Y | missense |
| 8 | 1 | ATRX | T/A | X:76845332 | 146 | 0.54 | p.E2063D | p.E2063D | missense |
| 16 | 1 | ATRX | G/A | X:76909629 | 87 | 0.62 | p.R1426* | p.R1426* | nonsense |
| 17 | 1 | ATRX | C/A | X:76937470 | 416 | 0.36 | p.R1093M | p.R1093M | missense |
| 8 | 1 | BCOR | T/C | X:39921444 | 25 | 0.4 | p.N1459S | p.N1459S | missense |
| 9 | 0 | BCOR | G/C | X:39931990 | 78 | 0.32 | p.T870S | p.T870S | missense |
| 17 | 1 | BCOR | G/T | X:39932971 | 184 | 0.49 | p.S543* | p.S543* | nonsense |
| 18 | 1 | BCOR | C/T | X:39934378 | 49 | 0.06 | p.R74H | p.R74H | missense |
| 1 | 0 | BCORL1 | G/C | X:129148345 | 85 | 0.49 | p.G533R | p.G533R | missense |
| 9 | 0 | BCORL1 | A/G | X:129149906 | 49 | 0.31 | p.K1053R | p.K1053R | missense |
| 15 | 1 | BLM | G/A | 15:91306241 | 214 | 0.43 | p.R643H | p.R643H | missense |
| 5 | 0 | BRCA2 | G/A | 13:32953550 | 228 | 0.33 | p.A2951T | p.A2951T | missense |
| 14 | 1 | BRIP1 | T/C | 17:59878659 | 68 | 0.5 | p.I365M | p.I365M | missense |
| 7 | 0 | CCND1 | A/G | 11:69465962 | 50 | 0.46 | p.D267G | p.D267G | missense |

TABLE 2B-continued

All Mutations Detected in Müllerian Adenosarcoma Sample

| case # | SO? | gene | Mutation | Position | Coverage | A.F. | canonical AA change | Best Effest AA change | type of mutation |
|---|---|---|---|---|---|---|---|---|---|
| 11 | 0 | CCND1 | A/G | 11:69462780 | 51 | 0.45 | p.N198S | p.N198S | missense |
| 12 | 0 | CD58 | T/C | 1:117061887 | 56 | 0.5 | p.I237V | p.I237V | missense |
| 7 | 0 | CDH1 | C/T | 16:68842734 | 112 | 0.48 | p.R224C | p.R224C | missense |
| 10 | 0 | CDK5 | C/T | 7:150752151 | 55 | 0.07 | p.G205S | p.G205S | missense |
| 1 | 0 | CHEK2 | C/A | 22:29091178 | 82 | 0.48 | p.D438Y | p.D481Y | missense |
| 18 | 1 | CIITA | G/C | 16:11000926 | 58 | 0.52 | p.R526P | p.R527P | missense |
| 8 | 1 | CREBBP | T/G | 16:3778424 | 46 | 0.43 | p.Q2208H | p.O2208H | missense |
| 12 | 0 | CRKL | G/A | 22:21288287 | 70 | 0.53 | p.V178I | p.V178I | missense |
| 3 | 0 | CUX1 | G/A | 7:101847695 | 26 | 0.12 | p.V978I | p.V989I | missense |
| 14 | 1 | CUX1 | C/G | 7:101921229 | 16 | 0.69 | p.L525V | p.L525V | missense |
| 3 | 0 | DICER1 | ATC/A | 14:95572398 | 174 | 0.08 | p.D989fs | p.D989fs | frameshift |
| 8 | 1 | DICER1 | T/A | 14:95560475 | 83 | 0.4 | p.E1705V | p.E1705V | missense |
| 11 | 0 | DIS3 | C/T | 13:73346400 | 85 | 0.66 | p.R467Q | p.R467O | missense |
| 5 | 0 | DMD | C/A | X:32563370 | 89 | 0.45 | p.E692* | p.E692* | nonsense |
| 10 | 0 | DMD | G/A | X:32490403 | 95 | 0.42 | p.R943C | p.R943C | missense |
| 9 | 0 | EP300 | A/G | 22:41522003 | 104 | 0.4 | p.M289V | p.M289V | missense |
| 16 | 1 | EP300 | G/C | 22:41573958 | 124 | 0.46 | p.L2081F | p.L2081F | missense |
| 9 | 0 | EPHA3 | A/G | 3:89445101 | 115 | 0.42 | p.Y474C | p.Y474C | missense |
| 1 | 0 | ERBB2 | G/A | 17:37872647 | 20 | 0.6 | p.R536Q | p.R536Q | missense |
| 8 | 1 | ERBB2 | C/A | 17:37884176 | 66 | 0.97 | p.A1216D | p.A1216D | missense |
| 9 | 0 | ERBB2 | C/G | 17:37881619 | 29 | 0.21 | p.R897G | p.R897G | missense |
| 9 | 0 | ERCC4 | TGGCCAA/T | 16:14020606 | 165 | 0.25 | p.PR194del | p.PR194del | indel |
| 13 | 0 | ERCC4 | C/T | 16:14028081 | 65 | 0.49 | p.P379S | p.P379S | missense |
| 11 | 0 | EXT2 | G/A | 11:44129620 | 120 | 0.48 | p.V120I | p.V153I | missense |
| 17 | 1 | EXT2 | G/A | 11:44228435 | 255 | 0.67 | p.E530K | p.E563K | missense |
| 18 | 1 | FAM46C | A/G | 1:118166331 | 244 | 0.36 | p.I281V | p.I281V | missense |
| 1 | 0 | FANCA | G/A | 16:89811469 | 43 | 0.53 | p.P1175L | p.P1175L | missense |
| 14 | 1 | FANCA | G/C | 16:89833576 | 83 | 0.28 | p.S858R | p.S858R | missense |
| 10 | 0 | FANCC | G/A | 9:98011497 | 86 | 0.5 | p.S26F | p.S26F | missense |
| 5 | 0 | FANCD2 | A/G | 3:10094159 | 97 | 0.52 | p.N545S | p.N545S | missense |
| 7 | 0 | FANCF | T/C | 11:22647287 | 42 | 0.55 | p.S24G | p.S24G | missense |
| 17 | 1 | FANCF | G/A | 11:22646800 | 196 | 0.31 | p.A186V | p.A186V | missense |
| 1 | 0 | FKBP9 | A/G | 7:33044881 | 127 | 0.09 | p.N544S | p.N597S | missense |
| 2 | 0 | FLT4 | G/A | 5:180045911 | 44 | 0.5 | p.P954S | p.P954S | missense |
| 11 | 0 | FLT4 | G/A | 5:180045911 | 34 | 0.56 | p.P954S | p.P954S | missense |
| 18 | 1 | GATA6 | G/A | 18:19751194 | 39 | 0.56 | p.R30Q | p.R30Q | missense |
| 8 | 1 | GLI2 | C/T | 2:121555015 | 54 | 0.57 | p.A40V | p.A40V | missense |
| 11 | 0 | GLI2 | G/A | 2:121555005 | 56 | 0.39 | p.V37M | | missense |
| 17 | 1 | GLI2 | C/A | 2:121746512 | 30 | 0.43 | p.R1008S | p.R1008S | missense |
| 4 | 0 | GLI3 | G/C | 7:42005073 | 33 | 0.42 | p.H1200D | p.H1200D | missense |
| 18 | 1 | GLI3 | T/C | 7:42007380 | 150 | 0.45 | p.I749V | p.I749V | missense |
| 1 | 0 | GNAS | C/G | 20:57430118 | 37 | 0.57 | p.R600G | p.R600G | missense |
| 2 | 0 | GSTM5 | C/T | 1:110257825 | 132 | 0.51 | p.A177V | p.A177V | missense |
| 5 | 0 | GSTM5 | C/T | 1:110257854 | 274 | 0.54 | p.R187C | p.R187C | missense |
| 6 | 0 | IGF1R | A/G | 15:99251301 | 72 | 0.47 | p.N202S | p.N202S | missense |
| 17 | 1 | IGF1R | A/C | 15:99500663 | 83 | 0.67 | p.T1366P | p.T1366P | missense |
| 14 | 1 | JAK2 | C/T | 9:5126729 | 54 | 0.33 | p.R1113C | p.R1113C | missense |
| 5 | 0 | KDM6A | TCTG/T | X:44929507 | 418 | 0.41 | p.L872del | p.L924del | indel |
| 9 | 0 | KDM6A | C/G | X:44870244 | 55 | 0.64 | p.F141L | p.F141L | missense |
| 1 | 0 | KDM6B | C/G | 17:7752322 | 23 | 0.7 | p.P906A | p.P906A | missense |
| 12 | 0 | KDM6B | T/G | 17:7752509 | 48 | 0.58 | p.V968G | p.V968G | missense |
| 10 | 0 | KDR | C/T | 4:55946257 | 50 | 0.1 | p.G1308R | p.G1308R | missense |
| 8 | 1 | KRAS | C/G | 12:25398284 | 133 | 0.45 | p.G12A | p.G12A | missense |
| 4 | 0 | MET | C/T | 7:116411923 | 165 | 0.45 | p.R970C | p.R988C | missense |
| 2 | 0 | MITE | C/A | 3:69987158 | 146 | 0.44 | p.S180R | p.S180R | missense |
| 11 | 0 | MLH1 | T/C | 3:37092186 | 51 | 0.51 | | p.L268P | missense |
| 4 | 0 | MLL | G/A | 11:118344200 | 120 | 0.15 | p.V776I | p.V776I | missense |
| 14 | 1 | MLL | C/T | 11:118344839 | 94 | 0.51 | p.L989F | p.L989F | missense |
| 16 | 1 | MLL | G/A | 11:118343378 | 185 | 0.39 | p.E502K | p.E502K | missense |
| 2 | 0 | MLL2 | G/A | 12:49434742 | 66 | 0.52 | p.P2271S | p.P2271S | missense |
| 6 | 0 | MLL2 | G/A | 12:49443634 | 102 | 0.51 | p.T1246M | p.T1246M | missense |
| 8 | 1 | MLL2 | TTGC/T | 12:49426905 | 54 | 0.07 | p.3860_3861QQ > Q | p.3860_3861QQ > Q | indel |
| 12 | 0 | MLL2 | C/T | 12:49431843 | 42 | 0.48 | p.R3099H | p.R3099H | missense |
| 6 | 0 | MSH6 | C/T | 2:48030603 | 103 | 0.45 | p.P1073S | p.P1073S | missense |
| 2 | 0 | MUTYH | T/C | 1:45796213 | 73 | 0.49 | p.Q495R | p.Q498R | missense |
| 8 | 1 | MYB | A/G | 6:135507111 | 159 | 0.43 | p.K32E | p.K32E | missense |
| 13 | 0 | NF1 | T/G | 17:29679341 | 70 | 0.06 | p.Y2508* | p.Y2508* | nonsense |
| 9 | 0 | NFKBIZ | G/C | 3:101570944 | 125 | 0.48 | p.G102A | p.G102A | missense |
| 18 | 1 | NFKBIZ | C/T | 3:101572512 | 273 | 0.33 | p.A381V | p.A381V | missense |
| 4 | 0 | NOTCH1 | T/C | 9:139391101 | 12 | 0.33 | p.S2364G | p.S2364G | missense |
| 2 | 0 | NOTCH2 | GC/AA | 1:120612013 | 32 | 0.17 | p.A3F | p.A3F | missense |
| 6 | 0 | NOTCH2 | A/T | 1:120468201 | 60 | 0.53 | p.L1413H | p.L1413H | missense |
| 9 | 0 | NOTCH2 | G/A | 1:120462933 | 67 | 0.07 | p.R1800C | p.R1800C | missense |
| 12 | 0 | NOTCH2 | T/C | 1:120469147 | 59 | 0.41 | p.D1327G | p.D1327G | missense |
| 16 | 1 | NOTCH2 | C/T | 1:120539653 | 59 | 0.58 | p.G240S | p.G240S | missense |

TABLE 2B-continued

All Mutations Detected in Müllerian Adenosarcoma Sample

| case # | SO? | gene | Mutation | Position | Coverage | A.F. | canonical AA change | Best Effest AA change | type of mutation |
|---|---|---|---|---|---|---|---|---|---|
| 3 | 0 | NTRK1 | G/A | 1:156837949 | 37 | 0.59 | p.R161H | p.R161H | missense |
| 17 | 1 | PAX5 | G/T | 9:37034001 | 39 | 0.13 | p.P10T | p.P10T | missense |
| 4 | 0 | PIK3C2B | C/A | 1:204426183 | 68 | 0.37 | p.A577S | p.A577S | missense |
| 14 | 1 | PIK3C2B | C/A | 1:204426183 | 46 | 0.33 | p.A577S | p.A577S | missense |
| 18 | 1 | PIK3C2B | CATT/C | 1:204438234 | 122 | 0.18 | p.N232del | p.N232del | indel |
| 11 | 0 | PIK3CA | G/A | 3:178921566 | 71 | 0.44 | p.D350N | p.D350N | missense |
| 8 | 1 | PIK3R1 | AGGTGGTTGACTCAAAAAGGTGTTC/A | 5:67591246 | 198 | 0.2 | p.M582_splice | p.M582_splice | splice site |
| 2 | 0 | PRAME | C/A | 22:22890642 | 97 | 0.44 | p.R459S | p.R459S | missense |
| 9 | 0 | PRAME | G/A | 22:22892314 | 74 | 0.42 | p.R263C | p.R263C | missense |
| 12 | 0 | PRAME | C/T | 22:22920869 | 48 | 0.58 | p.V384I | p.V384I | missense |
| 4 | 0 | PRDMI | G/A | 6:106536107 | 186 | 0.53 | p.R25K | p.R25K | missense |
| 3 | 0 | PRKDC | G/A | 8:48691334 | 74 | 0.07 | p.T3869M | p.T3869M | missense |
| 12 | 0 | PRKDC | T/C | 8:48762004 | 75 | 0.4 | p.M2356V | p.M2356V | missense |
| 12 | 0 | PRKDC | C/T | 8:48801111 | 78 | 0.47 | p.A1461T | p.A1461T | missense |
| 18 | 1 | PRKDC | C/T | 8:48691067 | 68 | 0.47 | p.G3936S | p.G3936S | missense |
| 5 | 0 | PRPF8 | A/C | 17:1560054 | 108 | 0.32 | p.L1836W | p.L1836W | missense |
| 1 | 0 | PTCH1 | G/A | 9:98231239 | 85 | 0.52 | p.R682C | p.R682C | missense |
| 8 | 1 | PTEN | CAAAT/C | 10:89720832 | 194 | 0.88 | p.A328fs | p.A328fs | frameshift |
| 18 | 1 | PTK2 | G/A | 8:141678499 | 113 | 0.54 | p.P912S | p.P934S | missense |
| 14 | 1 | PTPN11 | A/G | 12:112915526 | 24 | 0.96 | p.I309V | p.I309V | missense |
| 1 | 0 | RAD21 | C/T | 8:117879001 | 63 | 0.44 | | | intronic? |
| 11 | 0 | RARA | C/T | 17:38508234 | 79 | 0.41 | p.T181M | p.T181M | missense |
| 15 | 1 | RARA | C/G | 17:38487528 | 98 | 0.47 | p.P20A | p.P20A | missense |
| 12 | 0 | RB1 | C/T | 13:49033854 | 110 | 0.05 | p.T664I | p.T664I | missense |
| 13 | 0 | RET | C/T | 10:43604509 | 78 | 0.51 | p.S365L | p.S365L | missense |
| 18 | 1 | RET | G/A | 10:43620396 | 110 | 0.07 | p.S1002N | p.S1002N | missense |
| 12 | 0 | RFWD2 | C/G | 1:175957451 | 80 | 0.38 | p.A649P | p.A649P | missense |
| 5 | 0 | RHPN2 | G/T | 19:33490564 | 217 | 0.06 | p.L385I | p.L385I | missense |
| 1 | 0 | ROS1 | C/T | 6:117710875 | 142 | 0.55 | p.R466Q | p.R466Q | missense |
| 9 | 0 | ROS1 | G/A | 6:117686796 | 82 | 0.22 | p.A974V | p.A974V | missense |
| 10 | 0 | ROS1 | G/A | 6:117708799 | 59 | 0.39 | p.S653F | p.S653F | missense |
| 16 | 1 | RUNX1 | A/G | 21:36259324 | 22 | 0.82 | p.L29S | p.L56S | missense |
| 12 | 0 | SDHC | A/G | 1:161332224 | 61 | 0.07 | | p.K116R | missense |
| 13 | 0 | SDHC | G/C | 1:161332307 | 56 | 0.45 | | p.E144Q | missense |
| 12 | 0 | SETBP1 | C/T | 18:42530795 | 69 | 0.54 | p.P497L | p.P497L | missense |
| 3 | 0 | SF1 | C/G | 11:64535210 | 51 | 0.47 | p.G392A | p.G517A | missense |
| 16 | 1 | SF1 | C/CGGCGGA | 11:64533452 | 36 | 0.25 | p.586_586P > PPP | p.586_586P > PPP | indel |
| 17 | 1 | SH2B3 | T/C | 12:111872722 | 147 | 0.48 | | p.L6P | missense |
| 4 | 0 | SMARCA4 | G/A | 19:11144829 | 46 | 0.09 | p.V1302I | p.V1302I | missense |
| 8 | 1 | SMARCA4 | C/G | 19:11129654 | 38 | 0.39 | p.Y820* | p.Y820* | nonsense |
| 9 | 0 | SMARCB1 | C/G | 22:24143292 | 90 | 0.47 | | p.T166S | missense |
| 5 | 0 | SMC1A | A/G | X:53407557 | 116 | 0.31 | p.I1201T | p.I1201T | missense |
| 4 | 0 | SMO | G/A | 7:128843411 | 23 | 0.39 | p.R173H | p.R173H | missense |
| 13 | 0 | SMO | C/T | 7:128846362 | 79 | 0.06 | p.R400C | p.R400C | missense |
| 14 | 1 | SOX9 | C/T | 17:70120134 | 11 | 0.27 | p.A379V | p.A379V | missense |
| 10 | 0 | STAT6 | C/T | 12:57496683 | 226 | 0.04 | p.V412I | p.V461I | missense |
| 16 | 1 | TCF7L1 | GGGC/G | 2:85360828 | 10 | 0.7 | p.7_8GG > G | p.7_8GG > G | indel |
| 9 | 0 | TERT | G/A | 5:1293767 | 15 | 0.4 | p.H412Y | p.H412Y | missense |
| 1 | 0 | TET2 | G/T | 4:106196819 | 164 | 0.51 | p.V1718L | p.V1739L | missense |
| 9 | 0 | TET2 | G/T | 4:106196819 | 107 | 0.51 | p.V1718L | p.V1739L | missense |
| 16 | 1 | TP53 | C/A | 17:7577535 | 96 | 0.96 | p.R249M | p.R249M | missense |
| 18 | 1 | TP53 | AG/A | 17:7578191 | 77 | 0.58 | p.P219fs | p.P219fs | frameshift |
| 15 | 1 | TSC2 | G/T | 16:2134508 | 41 | 0.51 | p.A1429S | p.A1429S | missense |
| 17 | 1 | TSC2 | CCTT/C | 16:2134981 | 154 | 0.46 | p.F1510del | p.F1510del | indel |
| 7 | 0 | XPA | T/G | 9:100447273 | 115 | 0.47 | p.E202A | p.E202A | missense |
| 10 | 0 | ZNF217 | G/A | 20:52193660 | 144 | 0.53 | p.T548I | p.T548I | missense |

SO? = Associated with SO?; 1 = yes, 0 = no

TABLE 3A

Recurrent Gene-Level Copy Number Changes in Müllerian Adenosarcoma.

| | | Case Number | | | | | | | | | | | | | | | | | | |
|---|---|---|---|---|---|---|---|---|---|---|---|---|---|---|---|---|---|---|---|---|
| | | | | | | | | | | | | | | 14* | | | | 18* | | |
| Locus | Gene | 1 | 2 | 3 | 4 | 5 | 6 | 7 | 8* | 9 | 10 | 11 | 12 | 13 | −SO | +SO | 15* | 16* | 17* | −SO | +SO |
| 1p36.33 | PRKCZ | . | . | . | . | . | . | . | G | . | . | . | . | . | . | . | L | . | . | . | . |
| 1p36.22 | MTOR | . | . | . | . | . | . | . | G | . | . | . | . | . | . | . | L | . | . | . | . |

TABLE 3A-continued

Recurrent Gene-Level Copy Number Changes in Müllerian Adenosarcoma.

| | | Case Number | | | | | | | | | | | | | 14* | | | | | 18* | |
|---|---|---|---|---|---|---|---|---|---|---|---|---|---|---|---|---|---|---|---|---|---|
| Locus | Gene | 1 | 2 | 3 | 4 | 5 | 6 | 7 | 8* | 9 | 10 | 11 | 12 | 13 | −SO | +SO | 15* | 16* | 17* | −SO | +SO |
| 1p36.11 | ARID1A | . | . | . | . | . | . | . | . | . | . | . | . | . | L | L | L | . | . | . | . |
| 1p11.2 | NOTCH2 | . | . | . | . | . | . | . | . | . | . | . | . | . | . | . | G | G | . | G | G |
| 1q23.1 | NTRK1 | . | . | . | . | . | . | . | L | . | L | . | G | . | . | . | . | G | . | G | G |
| 1q23.3 | SDHC | . | . | . | . | . | . | . | G | . | . | . | . | . | . | . | . | G | . | G | G |
| 1q44 | AKT3 | . | . | . | . | . | . | . | . | . | . | . | . | . | . | . | G | . | L | . | . |
| 3p25.2 | RAF1 | . | . | . | . | . | . | . | . | . | . | . | . | . | . | . | . | . | L | G | G |
| 3p25.1 | XPC | . | . | . | . | . | . | . | . | . | . | . | . | . | . | . | . | . | L | G | G |
| 3p21.1 | BAP1 | . | . | . | . | . | . | . | . | . | . | . | L | . | . | . | . | . | L | L | L |
| 3p13 | MITF | . | . | . | . | . | . | . | . | . | . | . | . | . | . | . | . | . | L | L | L |
| 3q26.2 | MECOM | . | . | . | . | . | G | . | . | . | . | . | G | L | . | . | G | L | . | . | . |
| 3q26.32 | PIK3CA | . | . | . | . | . | . | G | . | . | . | . | . | . | . | . | . | . | . | G | G |
| 4p16.3 | FGFR3 | . | . | . | . | . | . | . | L | L | . | . | . | G | . | L | . | . | . | G | G |
| 4p13 | PHOX2B | . | . | . | . | . | . | . | L | L | . | . | . | . | . | . | . | . | . | G | G |
| 4q12 | KDR | . | . | . | . | . | . | . | . | . | . | . | G | . | . | . | . | . | . | G | G |
| 4q31.3 | FBXW7 | . | . | . | . | . | G | . | . | . | . | . | . | L | . | . | . | L | . | . | . |
| 5p15.33 | TERT | . | . | . | . | . | L | . | . | . | L | . | L | . | G | G | . | G | . | . | G |
| 5q11.2 | MAP3K1 | . | . | . | . | . | . | . | . | . | . | . | . | . | . | . | . | L | . | L | L |
| 5q13.1 | PIK3R1 | . | . | . | . | . | G | . | . | . | G | . | G | . | . | . | . | L | . | L | L |
| 5q35.2 | FGFR4 | . | . | . | . | . | . | . | . | . | . | . | G | . | . | L | . | . | . | L | L |
| 6p21.1 | CCND3 | . | . | . | . | . | . | . | . | . | . | . | G | . | G | . | . | G | . | . | . |
| 6q22.1 | ROS1 | . | . | . | . | . | . | . | . | . | . | L | L | . | . | . | . | L | . | G | G |
| 6q26 | PARK2 | . | . | . | . | . | . | . | . | . | . | L | . | . | . | . | . | . | . | G | G |
| 8p11.23 | FGFR1 | . | . | . | . | . | . | . | G | . | . | . | . | . | . | . | . | G | . | . | . |
| 8q13.1 | MYBL1 | . | . | . | . | . | . | G | . | . | . | . | G | L | L | . | G | . | G | . | . |
| 8q24.11 | RAD21 | . | . | . | . | . | . | . | . | . | . | . | G | . | . | . | G | L | . | . | . |
| 9p24.1 | JAK2 | . | . | . | L | . | . | . | . | . | . | . | . | . | L | . | L | L | . | . | . |
| 9p21.3 | CDKN2A | . | . | . | L | . | . | . | . | . | . | . | . | . | L | . | L | L | L | . | . |
| 9q22.33 | PTCH1 | . | . | . | . | . | . | . | . | . | G | . | . | . | L | L | . | . | . | . | . |
| 10q23.31 | PTEN | . | . | . | . | . | . | . | . | . | G | . | . | . | . | . | . | L | . | . | . |
| 11q13.3 | CCND1 | . | . | . | . | . | . | . | . | . | . | . | G | . | . | . | . | G | . | L | . |
| 12p13.32 | CCND2 | . | . | . | . | . | . | . | . | G | . | . | . | . | . | . | . | G | . | . | . |
| 12p13.2 | ETV6 | . | . | . | . | . | . | . | . | G | . | . | . | . | . | . | . | G | . | . | . |
| 12p12.1 | KRAS | . | . | . | . | . | . | . | . | . | . | . | . | . | . | . | G | G | . | . | . |
| 12q13.11 | ARID2 | . | . | . | . | . | . | G | . | . | . | . | L | . | . | . | . | G | . | . | . |
| 12q13.3 | CDK2 | . | . | . | . | . | . | . | G | . | . | . | . | . | . | . | . | . | . | L | L |
| 12q13.3 | ERBB3 | . | . | . | . | . | . | . | G | . | . | . | . | . | . | . | G | G | . | . | . |
| 12q13.3 | STAT6 | . | . | . | . | . | G | . | . | G | G | . | G | . | G | G | . | G | . | . | . |
| 12q14.1 | CDK4 | . | . | . | . | . | G | . | . | G | G | . | . | . | G | G | . | . | . | L | L |
| 12q15 | MDM2 | . | . | . | . | . | G | . | . | G | G | . | . | . | G | G | G | . | . | . | . |
| 12q24.12 | SH2B3 | . | . | . | . | . | . | . | . | . | . | . | . | . | L | L | . | G | . | . | . |
| 12q24.13 | PTPN11 | . | . | . | . | . | . | . | . | . | . | . | . | . | L | L | G | G | . | . | . |
| 12q24.31 | HNF1A | . | . | . | . | . | . | . | . | G | . | . | . | . | L | L | G | G | . | . | . |
| 13q12.3 | FLT3 | . | . | . | . | . | . | . | . | . | . | . | . | . | . | . | . | . | G | L | L |
| 13q12.3 | FLT1 | . | . | . | . | . | . | . | . | . | . | . | . | . | . | . | . | . | G | L | L |
| 13q13.1 | BRCA2 | . | . | . | . | . | . | . | . | . | . | . | . | . | . | . | . | . | G | L | L |
| 13q14.2 | RB1 | . | . | . | . | . | . | . | . | . | . | . | L | . | . | . | . | L | . | L | L |
| 15q15.1 | BUB1B | . | . | . | . | . | . | . | . | . | . | . | . | . | . | . | L | L | . | L | L |
| 15q21.1 | B2M | . | . | . | . | . | . | . | . | . | . | . | G | . | . | . | L | L | . | L | L |
| 16q24.3 | FANCA | . | . | . | . | . | . | . | . | . | . | . | G | . | G | G | L | . | . | . | . |
| 19q12 | CCNE1 | . | . | . | . | . | . | . | . | . | . | . | L | . | . | . | G | . | . | . | . |
| 22q11.21 | CRKL | . | . | . | . | . | . | . | . | . | . | . | . | . | G | G | . | . | . | L | L |
| 22q11.22 | MAPK1 | . | . | . | . | . | . | . | . | . | . | . | . | . | G | G | . | . | . | L | L |
| 22q11.23 | SMARCB1 | . | . | . | . | . | . | . | . | . | . | . | G | . | G | . | . | . | . | L | L |
| 22q12.1 | CHEK2 | . | . | . | . | . | . | . | . | . | . | . | G | . | . | G | G | . | . | L | L |

Asterisk in the column header indicates cases associated with sarcomatous overgrowth (SO).
G indicates a copy number gain while L indicates copy number loss.
Blank (empty) boxes indicate copy number neutral genes.

TABLE 3B

All Gene-Level Copy Number Changes in Müllerian Adenosarcoma

| | Study Case # | 1 | 2 | 3 | 4 | 5 | 6 | 7 | 8 | 9 | 10 | 11 | 12 | 13 | 14 | | 15 | 16 | 17 | 18 | |
|---|---|---|---|---|---|---|---|---|---|---|---|---|---|---|---|---|---|---|---|---|---|
| | # CNVs | 0 | 0 | 0 | 0 | 2 | 4 | 5 | 5 | 7 | 7 | 8 | 14 | 14 | 18 | 19 | 20 | 28 | 37 | 39 | 39 |
| 1p36.33 | PRKCZ | . | . | . | . | . | G | . | . | . | . | . | . | . | . | . | L | . | . | . | . |
| 1p36.22 | MTOR | . | . | . | . | . | G | . | . | . | . | . | . | . | . | . | L | . | . | . | . |
| 1p36.11 | ARID1A | . | . | . | . | . | . | . | . | . | . | . | . | . | L | L | L | . | . | . | . |
| 1p11.2 | NOTCH2 | . | . | . | . | . | . | . | . | . | . | . | . | . | . | . | G | G | . | G | G |

TABLE 3B-continued

All Gene-Level Copy Number Changes in Müllerian Adenosarcoma

| | Study Case # | 1 | 2 | 3 | 4 | 5 | 6 | 7 | 8 | 9 | 10 | 11 | 12 | 13 | 14 | | 15 | 16 | 17 | 18 | |
|---|---|---|---|---|---|---|---|---|---|---|---|---|---|---|---|---|---|---|---|---|---|
| | # CNVs | 0 | 0 | 0 | 0 | 2 | 4 | 5 | 5 | 7 | 7 | 8 | 14 | 14 | 18 | 19 | 20 | 28 | 37 | 39 | 39 |
| 1q23.1 | NTRK1 | . | . | . | . | . | . | . | . | L | . | L | . | G | . | . | . | G | . | G | G |
| 1q23.3 | SDHC | . | . | . | . | . | . | . | . | G | . | . | . | . | . | . | . | G | . | G | G |
| 1q23.3 | DDR | . | . | . | . | . | . | . | . | . | . | . | . | . | . | . | . | . | . | . | . |
| 1q32.1 | PIK3C2B | . | . | . | . | . | . | . | . | G | . | . | . | . | . | . | . | . | . | . | . |
| 1q32.1 | MDM4 | . | . | . | . | . | . | . | . | G | . | . | . | . | . | . | . | . | . | . | . |
| 1q43 | FH | . | . | . | . | . | . | . | . | . | . | . | . | . | . | . | . | . | L | . | . |
| 1q44 | AKT3 | . | . | . | . | . | . | . | . | . | . | . | . | . | . | . | G | . | L | . | . |
| 2p23.3 | DNMT3A | . | . | . | . | . | . | . | . | . | . | . | . | . | . | . | . | . | . | G | G |
| 2p23.2 | ALK | . | . | . | . | . | . | . | . | . | . | . | . | . | . | . | . | . | . | G | G |
| 2q32.2 | PMS1 | . | . | . | . | . | . | . | . | . | . | . | . | . | G | G | . | . | . | . | . |
| 3p25.3 | VHL | . | . | . | . | . | . | . | . | . | . | . | . | . | . | . | . | . | L | . | . |
| 3p25.2 | RAF1 | . | . | . | . | . | . | . | . | . | . | . | . | . | . | . | . | . | L | G | G |
| 3p25.1 | XPC | . | . | . | . | . | . | . | . | . | . | . | . | . | . | . | . | . | L | G | G |
| 3p22.2 | MLH1 | . | . | . | . | . | . | . | . | . | . | . | . | . | . | . | . | . | L | . | . |
| 3p22.2 | MYD88 | . | . | . | . | . | . | . | . | . | . | . | . | . | . | . | . | . | L | . | . |
| 3p22.1 | CTNNB1 | . | . | . | . | . | . | . | . | . | . | . | . | . | . | . | . | . | L | . | . |
| 3p21.31 | SETD2 | . | . | . | . | . | . | . | . | . | . | . | . | . | . | . | . | . | L | . | . |
| 3p21.1 | BAP1 | . | . | . | . | . | . | . | . | . | . | L | . | . | . | . | . | . | L | L | L |
| 3p13 | MITF | . | . | . | . | . | . | . | . | . | . | . | . | . | . | . | . | . | L | L | L |
| 3p11.1 | EPHA3 | . | . | . | . | . | . | . | . | . | . | . | . | . | . | . | . | . | L | . | . |
| 3q12.3 | NFKBIZ | . | . | . | . | . | . | . | . | . | . | . | . | . | . | . | . | . | L | . | . |
| 3q13.11 | CBLB | . | . | . | . | . | . | . | . | . | . | . | . | . | . | . | . | . | L | . | . |
| 3q22.3 | STAG1 | . | . | . | . | . | . | . | . | . | . | . | . | . | . | . | . | . | . | . | . |
| 3q26.2 | MECOM | . | . | . | . | . | G | . | . | . | . | . | G | L | . | . | G | L | . | . | . |
| 3q26.32 | PIK3CA | . | . | . | . | . | . | . | G | . | . | . | . | . | . | . | . | . | . | G | G |
| 3q26.33 | SOX2 | . | . | . | . | . | . | . | . | . | . | . | . | . | . | . | . | . | L | . | . |
| 3q27.2 | ETV5 | . | . | . | . | . | . | . | . | . | . | . | . | . | . | . | . | . | L | . | . |
| 3q27.3 | BCL6 | . | . | . | . | . | . | . | . | . | . | . | . | . | . | . | . | . | L | . | . |
| 4p16.3 | FGFR3 | . | . | . | . | . | . | . | . | L | L | . | . | G | . | L | . | . | . | G | G |
| 4p13 | PHOX2B | . | . | . | . | . | . | . | . | L | L | . | . | . | . | . | . | . | . | G | G |
| 4q12 | PDGFRA | . | . | . | . | . | . | . | . | . | . | . | . | . | . | . | . | . | . | G | G |
| 4q12 | KIT | . | . | . | . | . | . | . | . | . | . | . | . | . | . | . | . | . | . | G | G |
| 4q12 | KDR | . | . | . | . | . | . | . | . | . | . | . | G | . | . | . | . | . | . | G | G |
| 4q24 | TET2 | . | . | . | . | . | . | . | . | . | . | . | . | . | . | . | . | L | . | . | . |
| 4q31.3 | FBXW7 | . | . | . | . | G | . | . | . | . | . | . | . | L | . | . | . | L | . | . | . |
| 5p15.33 | TERT | . | . | . | . | . | G | . | . | . | L | . | L | . | G | G | . | G | . | . | G |
| 5q11.2 | MAP3K1 | . | . | . | . | . | . | . | . | . | . | . | . | . | . | . | . | L | . | L | L |
| 5q13.1 | PIK3R1 | . | . | . | . | . | G | . | . | . | G | . | G | . | . | . | L | . | L | L | L |
| 5q22.1 | APC | . | . | . | . | . | . | . | . | . | . | . | . | . | . | . | . | . | . | L | L |
| 5q32 | PDGFRB | . | . | . | . | . | . | . | . | . | . | . | . | . | . | . | . | . | . | L | L |
| 5q35.1 | NPM1 | . | . | . | . | . | . | . | . | . | . | . | . | . | . | . | . | . | . | L | L |
| 5q35.2 | FGFR4 | . | . | . | . | . | . | . | . | . | . | . | . | G | . | L | . | . | . | L | L |
| 5q35.3 | FLT4 | . | . | . | . | . | . | . | . | . | . | . | . | . | . | . | . | . | . | . | . |
| 6p21.1 | CCND3 | . | . | . | . | . | . | . | . | . | . | . | . | G | G | . | . | G | . | . | . |
| 6q22.1 | ROS1 | . | . | . | . | . | . | . | . | . | . | . | L | L | . | . | . | L | . | G | G |
| 6q25.3 | ARID1B | . | . | . | . | . | . | . | . | . | . | . | L | . | . | . | . | . | . | . | . |
| 6q26 | PARK2 | . | . | . | . | . | . | . | . | . | . | . | L | . | . | . | . | . | . | G | G |
| 7p21.2 | ETV1 | . | . | . | . | . | . | . | . | . | . | . | . | . | . | . | . | . | G | . | . |
| 8p11.23 | FGFR1 | . | . | . | . | . | . | . | G | . | . | . | . | . | . | . | . | . | G | . | . |
| 8q13.1 | MYBL1 | . | . | . | . | . | . | . | G | . | . | . | G | L | L | . | G | . | G | . | . |
| 8q24.11 | RAD21 | . | . | . | . | . | . | . | . | . | . | . | G | . | . | . | G | L | . | . | . |
| 9p24.1 | JAK2 | . | . | . | . | L | . | . | . | . | . | . | . | . | . | L | L | L | . | . | . |
| 9p21.3 | CDKN2A | . | . | . | . | L | . | . | . | . | . | . | . | . | . | L | L | L | L | . | . |
| 9p21.3 | CDKN2B | . | . | . | . | . | . | . | . | . | . | . | . | . | . | . | . | . | L | . | . |
| 9p13.3 | FANCG | . | . | . | . | . | . | . | . | . | . | . | . | . | . | . | . | . | L | . | . |
| 9p13.2 | PAX5 | . | . | . | . | . | . | . | . | . | . | . | . | . | . | . | . | . | L | . | . |
| 9q21.2 | GNAQ | . | . | . | . | . | . | . | . | . | . | . | . | . | . | . | . | . | L | . | . |
| 9q21.33 | NTRK2 | . | . | . | . | . | . | . | . | . | . | . | . | . | . | . | . | . | L | . | . |
| 9q22.2 | SYK | . | . | . | . | . | . | . | . | . | . | . | . | . | . | . | . | . | L | . | . |
| 9q22.32 | FANCC | . | . | . | . | . | . | . | . | . | . | . | . | . | . | . | . | . | L | . | . |
| 9q22.32 | PTCH1 | . | . | . | . | . | . | . | . | . | . | . | . | . | . | . | . | . | L | . | . |
| 9q22.33 | XPA | . | . | . | . | . | . | . | . | . | . | . | . | . | . | . | . | . | L | . | . |
| 9q34.11 | CDK9 | . | . | . | . | . | . | . | . | . | . | . | . | . | . | . | . | . | L | . | . |
| 9q34.12 | ABL1 | . | . | . | . | . | . | . | . | . | . | . | . | . | . | . | . | . | L | . | . |
| 9q34.13 | TSC1 | . | . | . | . | . | . | . | . | . | . | . | . | . | . | . | . | . | L | . | . |
| 9q34.3 | NOTCH1 | . | . | . | . | . | . | . | . | . | . | . | . | . | . | . | . | . | L | . | . |
| 9q21.33 | NTRK2 | . | . | . | . | . | . | . | . | . | . | . | . | . | L | L | . | . | . | . | . |
| 9q22.31 | SYK | . | . | . | . | . | . | . | . | . | . | . | . | . | L | L | . | . | . | . | . |
| 9q22.33 | PTCH1 | . | . | . | . | . | . | . | . | . | G | . | . | . | L | L | . | . | L | . | . |
| 10q23.31 | PTEN | . | . | . | . | . | . | . | . | . | . | . | G | . | . | . | . | G | . | . | . |
| 11q13.3 | CCND1 | . | . | . | . | . | . | . | . | . | . | . | . | G | . | . | . | G | . | L | . |
| 12p13.32 | CCND2 | . | . | . | . | . | . | . | . | G | . | . | . | . | . | . | . | G | . | . | . |
| 12p13.2 | ETV6 | . | . | . | . | . | . | . | . | G | . | . | . | . | . | . | . | G | . | . | . |
| 12p12.1 | KRAS | . | . | . | . | . | . | . | . | . | . | . | . | . | . | . | G | G | . | . | . |
| 12q13.11 | ARID2 | . | . | . | . | . | . | . | G | . | . | . | . | . | L | . | G | . | . | . | . |

TABLE 3B-continued

All Gene-Level Copy Number Changes in Müllerian Adenosarcoma

| | | 1 | 2 | 3 | 4 | 5 | 6 | 7 | 8 | 9 | 10 | 11 | 12 | 13 | 14 | | 15 | 16 | 17 | 18 | |
|---|---|---|---|---|---|---|---|---|---|---|---|---|---|---|---|---|---|---|---|---|---|
| Study Case # / # CNVs | | 0 | 0 | 0 | 0 | 2 | 4 | 5 | 5 | 7 | 7 | 8 | 14 | 14 | 18 | 19 | 20 | 28 | 37 | 39 | 39 |
| 12q13.12 | MLL2 | . | . | . | . | . | . | . | . | . | . | . | . | . | . | . | . | G | . | . | . |
| 12q13.3 | CDK2 | . | . | . | . | . | . | . | . | G | . | . | . | . | . | . | . | . | . | L | L |
| 12q13.3 | ERBB3 | . | . | . | . | . | . | . | . | G | . | . | . | . | . | . | G | G | . | . | . |
| 12q13.3 | STAT6 | . | . | . | . | . | G | . | . | . | G | G | . | G | . | . | . | G | . | . | . |
| 12q14.1 | CDK4 | . | . | . | . | . | G | . | . | . | G | G | . | . | G | G | . | . | . | L | L |
| 12q15 | MDM2 | . | . | . | . | . | G | . | . | . | G | G | . | . | G | G | G | . | . | . | . |
| 12q24.12 | SH2B3 | . | . | . | . | . | . | . | . | . | . | . | . | . | L | L | . | G | . | . | . |
| 12q24.13 | PTPN11 | . | . | . | . | . | . | . | . | . | . | . | . | . | L | L | G | G | . | . | . |
| 12q24.31 | HNF1A | . | . | . | . | . | . | . | . | . | . | G | . | . | L | L | G | G | . | . | . |
| 13q12.3 | FLT3 | . | . | . | . | . | . | . | . | . | . | . | . | . | . | . | . | . | G | L | L |
| 13q12.3 | FLT1 | . | . | . | . | . | . | . | . | . | . | . | . | . | . | . | . | . | G | L | L |
| 13q13.1 | BRCA2 | . | . | . | . | . | . | . | . | . | . | . | . | . | . | . | . | . | G | L | L |
| 13q14.2 | RB1 | . | . | . | . | . | . | . | . | . | . | . | L | . | . | . | L | . | . | L | L |
| 15q15.1 | BUB1B | . | . | . | . | . | . | . | . | . | . | . | . | . | L | L | . | . | . | L | L |
| 15q21.1 | B2M | . | . | . | . | . | . | . | . | . | . | G | . | . | L | L | . | . | . | L | L |
| 15q25.3 | NTRK3 | . | . | . | . | . | . | . | . | . | . | . | . | . | . | . | . | . | . | G | G |
| 16q24.3 | FANCA | . | . | . | . | . | . | . | . | . | . | . | G | . | G | G | L | . | . | . | . |
| 19q12 | CCNE1 | . | . | . | . | . | . | . | . | . | . | . | L | . | . | . | G | . | . | . | . |
| 22q11.21 | CRKL | . | . | . | . | . | . | . | . | . | . | . | G | G | . | . | . | . | . | L | L |
| 22q11.22 | MAPK1 | . | . | . | . | . | . | . | . | . | . | . | G | G | . | . | . | . | . | L | L |
| 22q11.23 | SMARCB1 | . | . | . | . | . | . | . | . | . | . | . | G | G | . | . | . | . | . | L | L |
| 22q12.1 | CHEK2 | . | . | . | . | . | . | . | . | . | . | G | . | G | G | . | . | . | . | L | L |

Figure 2:
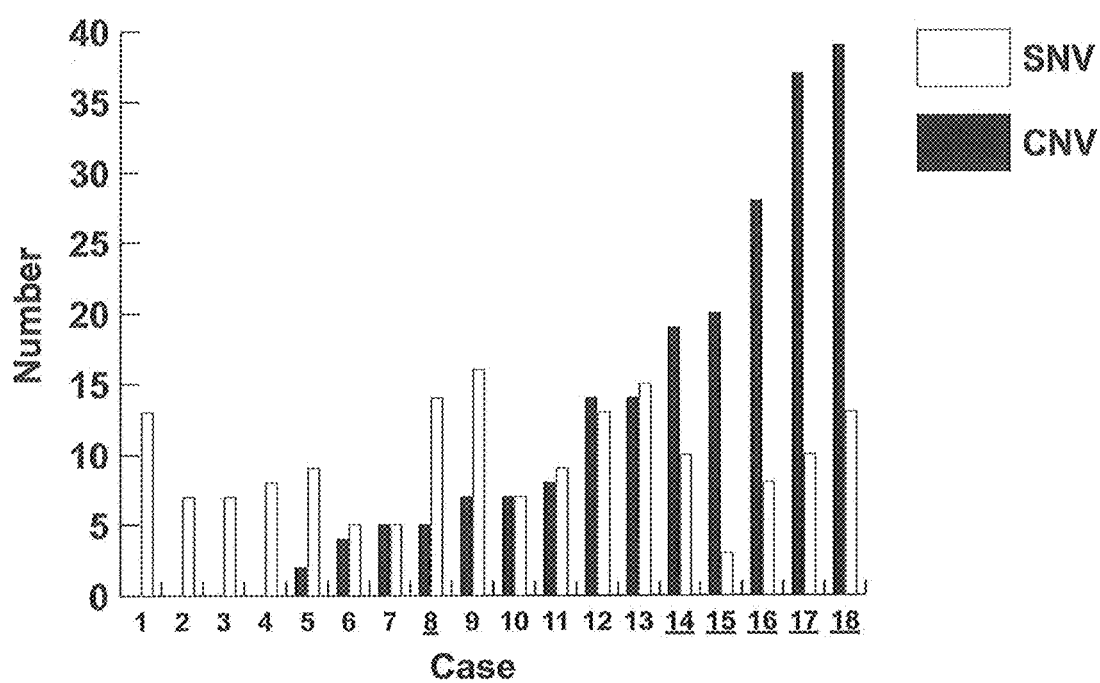
FIG. 2: Quantification of Genomic Alterations in Müllerian Adenosarcoma. The number of CNVs (black bars) and SNVs (grey bars) are graphically represented for each case of MA. The 6 cases of MA with SO are indicated by underlined numbers.

In quantifying CNV changes per case, a higher rate of CNVs in MA with SO (mean 24.6; range 5-39) compared to MA without SO (mean 5; range 0-14, p=0.0002; FIG. 2) was observed. With respect to CNV gains versus losses, MA without SO tended to have more gains (67%) compared to losses (33%), while MA with SO was more likely to have a predominance of CNV loss (58% versus 42%). In contrast to the distinct increase in CNV changes seen in MA associated with SO, when considering the frequency of mutation, the mean number of SNVs detected in MA with SO (mean 9.7; range 3-14) did not differ significantly from MA without SO (mean 9.5; range 3-14; p=0.5; FIG. 2). 162 mutations were identified across all 18 cases (the 2 samples with matched SO areas were each counted as one). Missense mutations were the most common (n=141; 87%), followed by small insertions and deletions (indels; n=8; 5%), nonsense (n=6; 3.7%), and frameshift (n=5; 3%) mutations. Two splice site mutations were also identified. Of the 147 missense and nonsense mutations, 98 (67%) were transitions and 49 (33%) were transversions.

Example 3

Single Nucleotide Variations in Tumor Suppressor Genes

Two (11%) MA had TP53 mutations (p.R249M, case 16; p.P219fs, case 18), both of which were samples associated with SO, representing 33% of all MA cases with SO. All cases were evaluated for TP53 protein expression with p53 immunohistochemistry. p53 overexpression was present in one case (case 16) that had a TP53 missense mutation (FIG. 3A), but case 18, which harbored a TP53 frameshift mutation, revealed complete loss of p53 expression, consistent with a null immunophenotype (FIG. 3B) in both areas with and without SO. All other MA demonstrated heterogeneous, scattered p53 positive cells, consistent with the wild type pattern of expression (FIG. 3C).

ATRX, which encodes a chromatin remodeling protein, was mutated in 3/18 (17%), representing 50% of the cases associated with SO. One was a nonsense mutation (p.R1426*; case 16), and the other two were missense mutations (p.E2063D, case 8; p.R1093M case 17). As loss of ATRX expression by immunohistochemistry has prognostic significance in other tumor types (23, 24), ATRX IHC was performed on all MA cases. Case 16, which harbored a nonsense mutation, showed complete loss of ATRX expression in tumor cells (FIG. 3D), but all other cases had intact nuclear expression (FIG. 3E), including the two cases (cases 8, 17) with missense mutations (FIG. 3F). Although there is ATRX protein expression in these 2 cases, it is not known whether the mutated gene products properly functioned in the tumor cells of these cases. It is interesting to note that case 16, which harbored the nonsense ATRX mutation, had a subsequent distant metastasis. Finally, it is unlikely that the ATRX nonsense mutation represents a germline event given its expression in normal tissues such as endothelial cells.

Example 4

Gene Level Copy Number Gains in Oncogenes

MYBL1

CNV gains of MYBL1, located on 8q13.1 (FIG. 4A), were identified in 4 MA (cases 8, 12, 15, and 17), including 3/6 (50%) associated with SO. MYBL1 IHC was performed on all MA cases, and in 3/4 cases with MYBL1 CNV gains, MYBL1 was strongly expressed in a subset of tumor cells (FIG. 4B), both in areas with and without SO, but one case was immunonegative for MYBL1. One case (case 7) without MYBL1 amplification showed scattered positivity (FIG. 4C).

MDM2 and CDK4

Figure 5A:
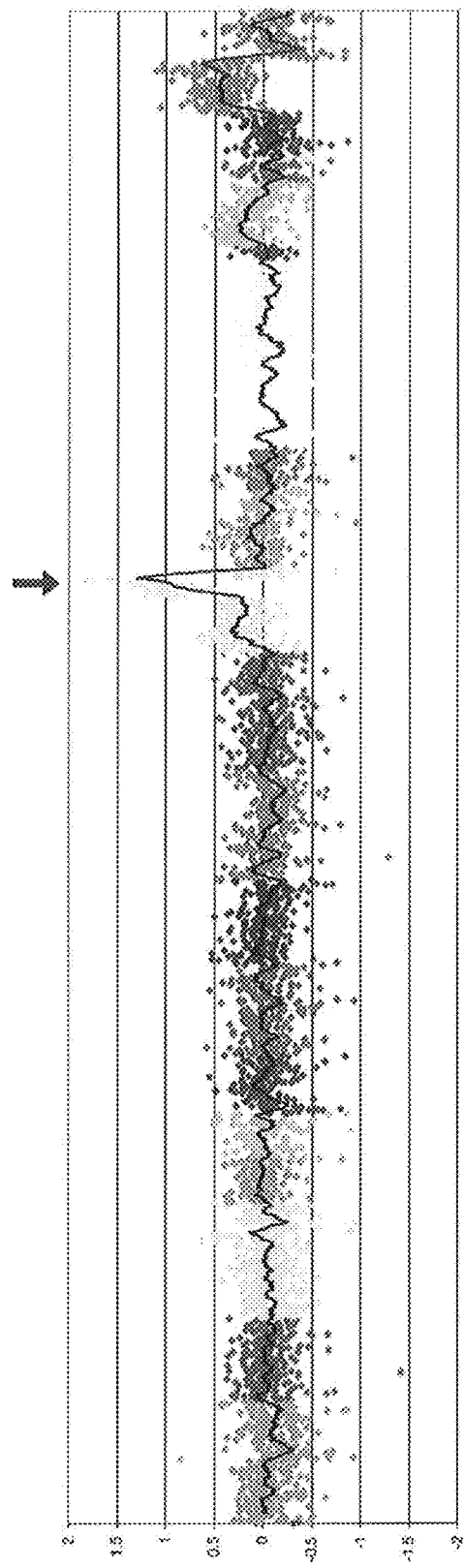
Figures 5D, 5E:
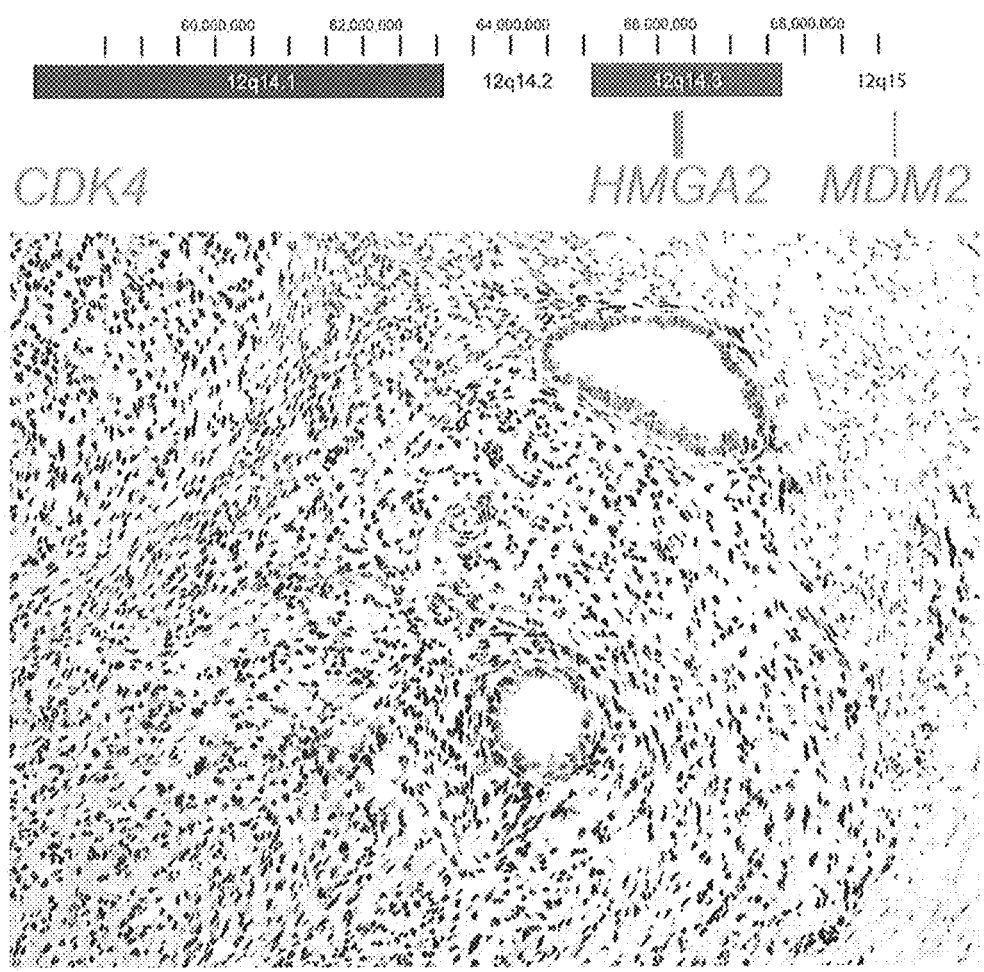
Figure 5F:
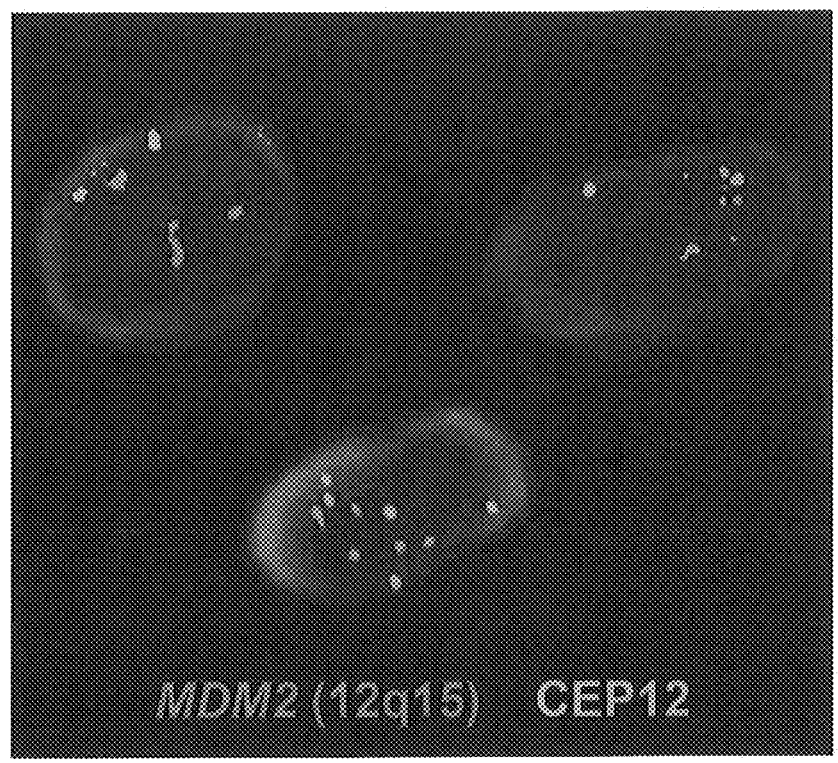

MDM2 and CDK4 copy number gains were present in 5 tumors (28%; FIG. 5A), including 3 MA without SO (cases 7, 10, and 11) and 2 MA with SO (cases 14 and 15). Increased expression of MDM2 and CDK4 by immunohistochemistry was present in all cases with copy number gains by CNV analysis, characterized by focal (n=1) or diffuse (>50%; n=4), weak to moderate (1-2+) CDK4 (FIG. 5B) and focal (n=5) moderate to strong (2-3+) MDM2 expression; FIG. 5C). In the 2 MA with SO, there was no difference in the MDM2 and CDK4 staining patterns between areas with and without SO. MDM2 amplification was confirmed by FISH in 2 cases (cases 10 and 14; FIG. 5F). HMGA2, a gene located on 12q14.3, in between MDM2 and CDK4 was not included in the targeted assay, but given its proximity to MDM2 (FIG. 5D) and its known involvement in translocations in many mesenchymal tumors, HMGA2 immunohistochemistry was evaluated in all tumors. HMGA2 was diffusely (>50%) and strongly (3+) positive in 4/5 tumors that contained low level amplification of MDM2 and CDK4 (FIG. 5E) and one tumor that did not have MDM2 and CDK4 amplification (case 16), with no difference in staining between areas with and without SO.

Example 5

Gene Level Copy Number Loss in Tumor Suppressor Genes

Five (28%) cases (1 without SO and 4 with SO) were associated with loss of CDKN2A by copy number analysis (cases 5, 14, 15, 16, and 17; Table 3). BAP1 and RB1 losses were present in 3 MA each (cases 12, 17, and 18 for BAP1 and 13, 16, and 18 for Rill). No CNVs were detected in TP53.

Example 6

Comparison of MA with and without SO

In two cases (cases 14 and 18), matched tumor samples with and without SO were independently analyzed and compared (FIG. 6). Tumor regions with SO tended to have slightly more CNV changes than regions without SO from the same individual across the genomic sequences interrogated, but these changes were not consistent between cases. Likewise, most missense mutations detected in one sample were also present in its matched pair. In one paired case (case 14), 10 SNVs were identified; 2 were present only in the typical MA area and one was present only in the SO region (Table 4). The other paired sample (case 18) had 13 SNVs detected, one of these was present only in the area of typical MA histology (Table 5).

TABLE 4

Mutations Identified in Case 14

| Gene | Mutation | Chromosomal Position | Amino Acid Change |
| --- | --- | --- | --- |
| ABL1 | G/A | 9:133759793 | p.G706S |
| APC | A/G | 5:112174643 | p.N1118D |
| BRIP1 | T/C | 17:59878659 | p.I365M |
| CUX1 | C/G | 7:101921229 | p.L525V |
| FANCA | G/C | 16:89833576 | p.S858R |
| JAK2 | C/T | 9:5126729 | p.R1113C |
| MLL | C/T | 11:118344839 | p.L989F |
| PIK3C2B | C/A | 1:204426183 | p.A577S |
| PTPN11 | A/G | 12:112915526 | p.I309V |
| SOX9 | C/T | 17:70120134 | p.A379V |

Mutations Identified in Case 14, with comparison of single nucleotide variations in areas of sarcomatous overgrowth (SO) versus areas lacking overt SO. Mutations present only in SO samples: CUX1, mutations present only in the sample without overt SO: ABL1 and SOX9, all other mutations identified in both components.

TABLE 5

Mutations Identified in Case 18

| Gene | Mutation | Chromosomal Position | Amino Acid Change |
| --- | --- | --- | --- |
| ARID2 | C/T | 12:46243365 | p.T573M |
| ASXL1 | G/T | 20:31022443 | p.G643V |
| BCOR | C/T | X:39934378 | p.R74H |
| CIITA | G/C | 16:11000926 | p.R526P |
| FAM46C | A/G | 1:118166331 | p.I281V |
| GATA6 | G/A | 18:19751194 | p.R30Q |
| GLI3 | T/C | 7:42007380 | p.I749V |
| NFKBIZ | C/T | 3:101572512 | p.A381V |
| PIK3C2B | CATT/C | 1:204438234 | p.N232del |
| PRKDC | C/T | 8:48691067 | p.G3936S |
| PTK2 | G/A | 8:141678499 | p.P912S |
| RET | G/A | 10:43620396 | p.S1002N |
| TP53 | AG/A | 17:7578191 | p.P219fs |

Table 5. Mutations Identified in Case 18, with comparison of single nucleotide variations in areas of sarcomatous overgrowth (SO) versus areas lacking overt SO. Mutations present only in the sample without overt SO: BCOR, all other mutations identified in both components.

Example 7

Cell Signaling Pathways Affected in MüLlerian Adenosarcoma

PIK3-AKT/PTEN Pathway

Some MA appears to have mutations of signaling pathways described in endometrial adenocarcinoma and other types of cancer, most notably the PIK3-AKT/PTEN pathway. The PIK3-AKT/PTEN pathway was affected in 13/18 (72%), including 4/6 (67%) MA with SO and 9/12 (75%) MA without SO. One case had a PTEN copy number gain (case 12), but loss of one PTEN copy was found in 1 MA (case 16), and a third case had a PTEN frameshift mutation (p.A328fs, case 8). AKT1 missense mutations were present in 3 MA (cases 3, 5, and 9), all without SO. PIK3CA copy number gains were identified in 2 cases, both with SO (cases 8 and 18), and 1 case had a PIK3CA missense mutation (case 11). PIK3R1 gains were observed in 3 cases (cases 6, 10, 12) all without SO; in contrast, 2 cases with SO (cases 16, 18) had PIK3R1 loss, and 1 MA (case 8) had a PIK3R1 splice site mutation (p.M582 splice). PIK3C2B copy number gain was found in 1/18 (case 9), 2 cases had PIK3C2B missense mutations (cases 4, 14), and one had a small deletion (case 18; p.N232del). ERBB2 missense mutations were identified in 3 MA (cases 1, 8, and 9). Finally, PDGFRB CNV loss was noted in 1/18 (case 18).

Example 8

Cytogenetic Abnormalities in Müllerian Adenosarcoma

Figure 7A:
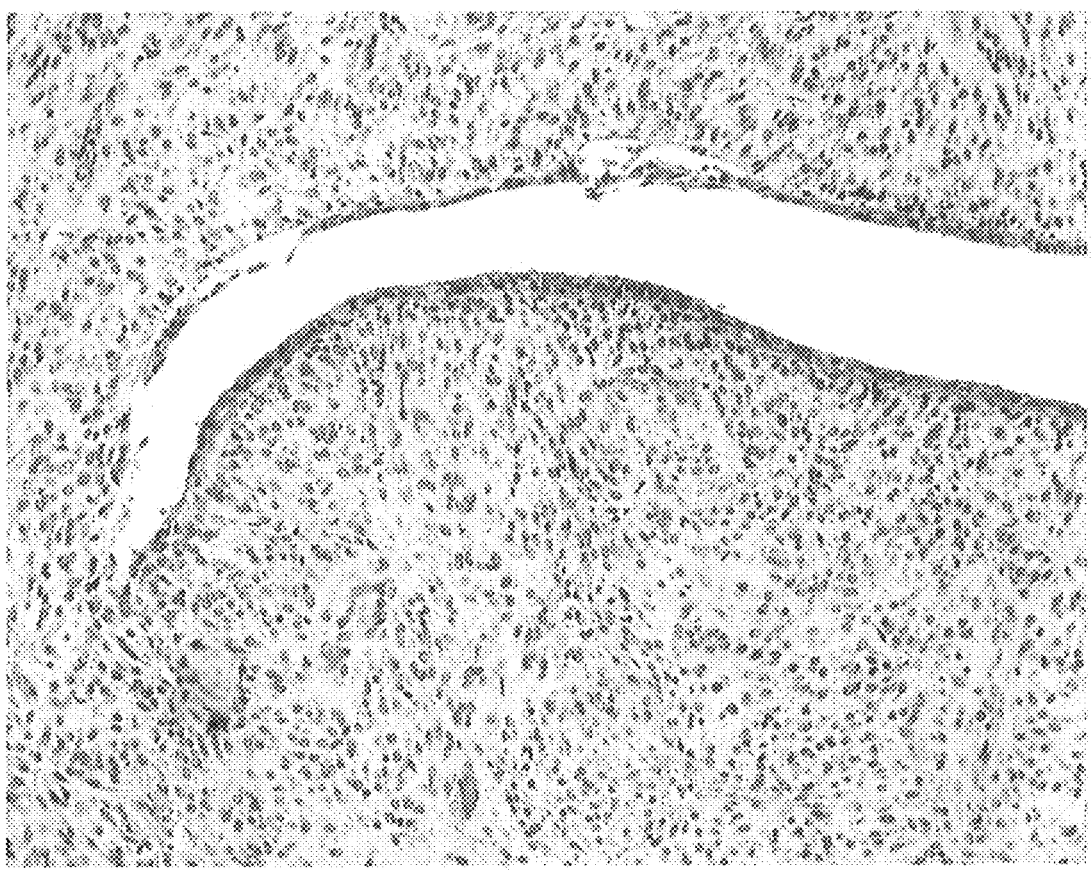
FIGS. 7A-C. Histologic features of Mullerian adenosarcoma (MA). A: MA is characterized by broad papillary projections of malignant stroma lined by benign epithelium (case 1). B: MA with sarcomatous overgrowth is characterized by >25% of the tumor lacking any epithelial component (case 6). C: Metastatic sarcoma to the lung (lung parenchyma shown in lower right hand corner) lacks any epithelial component (case 9).
Figure 7B:
Figure 7C:
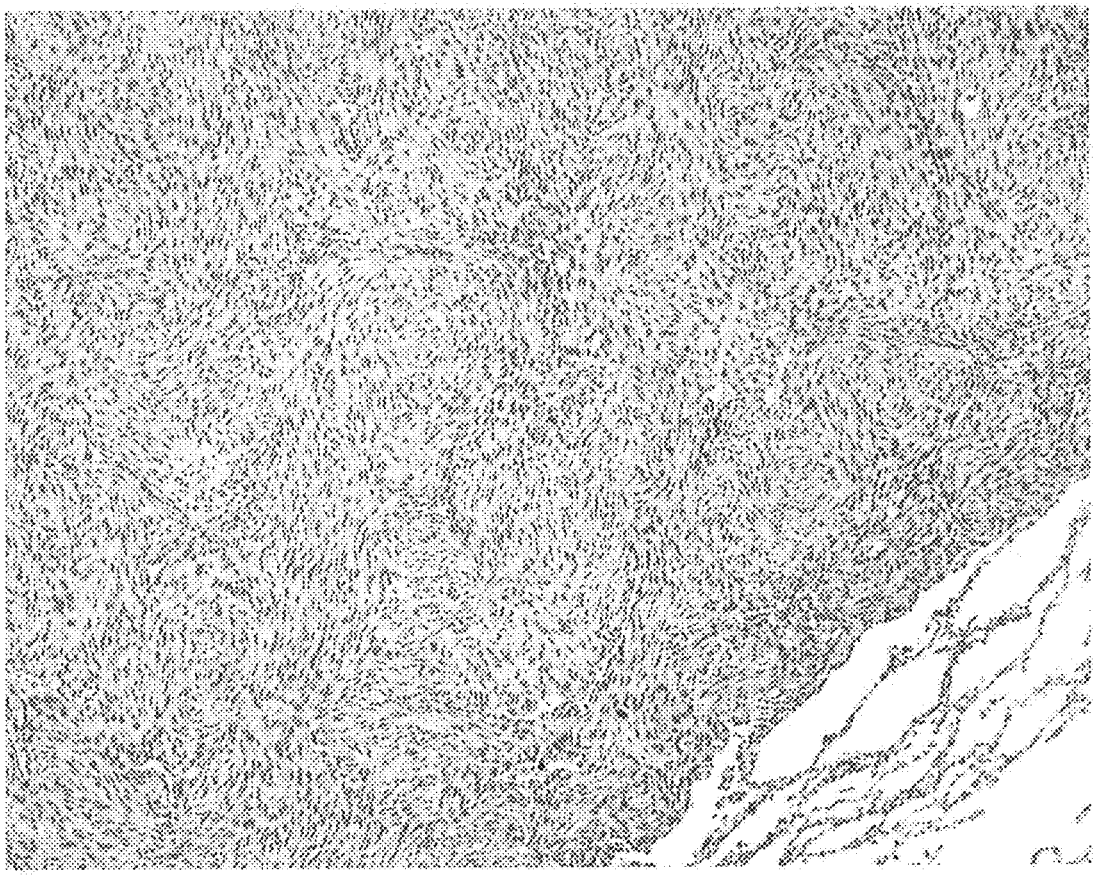

Samples (n=21 from 20 subjects; mean age 62 years, median age 65 years; range 26-82 years) included 15 primary MA (seven without SO (FIG. 7A), eight with SO (FIG. 7B), and six metastatic MA (sarcomatous component only) (FIG. 7C). This series comprises 13 primary uterine tumors (12 corpus, 1 cervical), 2 primary pelvic/abdominal (1 ovarian, 1 arising in endometriosis in the colon), 5 recurrent or metastatic tumors involving the abdomen and/or retroperitoneum, and 1 metastatic tumor in the lung. Two of the samples were from the same subject; the first was a primary MA with SO (case 10) and the second was a metastatic MA to the lung (case 9) approximately three years after the hysterectomy. The clinical and pathologic features of cases included in this series are summarized in Table 5.

TABLE 5

Clinical and pathologic characteristics of study cohort

| Case # | Age | Primary, recurrent, or metastatic tumor | Tumor location (anatomic) | Sarcomatous overgrowth | Depth of invasion | Associated with endometriosis, adenomyosis, endometrial polyps? | HRT or tamoxifen use? |
|---|---|---|---|---|---|---|---|
| 1 | 50 | primary | uterus endometrium | absent | 0 | yes-endometrial polyps | no |
| 2 | 77 | primary | endometrial polyps (multifocal) | absent | 0 | yes-endometrial polyps | yes |
| 3 | 65 | metastatic | abdomen/retroperitoneum | N/A | N/A | no | no |
| 4 | 73 | metastatic | bladder/pelvis (prior endometrial primary) | N/A | N/A | no | no |
| 5 | 61 | primary | uterus endometrium | present | 55% | yes endometrial polyps and adenomyosis | no |
| 6 | 70 | primary | uterus endometrium | present | 90% | no | no |
| 7 | 57 | primary | uterus endometrium | absent | 40% | no | no |
| 8 | 65 | primary | uterus endometrium | present | 10% | no | yes |
| 9 | 56 | metastatic | lung (prior endometrial primary) | N/A | N/A | no | no |
| 10 | 53 | primary | uterus endometrium | present | 60% | no | N/A (same subject as case #9) |
| 11 | 26 | primary | uterus endometrium | absent | 90% | yes-endometriosis | no |
| 12 | 65 | primary | pelvis (endometriosis-associated) | absent | N/A | yes-endometriosis | yes |
| 13 | 69 | primary | uterus endometrium | present | 30% | no | yes |
| 14 | 53 | primary | abdomen (endometriosis-associated) | absent | N/A | yes-endometriosis | no |
| 15 | 65 | primary | uterus endometrium | present | 40% | yes-adenomyosis | yes |
| 16 | 75 | recurrrent | pelvis (prior ovarian primary) | N/A | N/A | no | no |
| 17 | 61 | primary | uterus endometrium | absent | 50% | yes-adenomyosis | yes |
| 18 | 82 | metastatic | abdomen/retroperitoneum (prior endometrial primary) | N/A | N/A | no | unknown |
| 19 | 54 | primary | uterus cervical | present | 90% | no | no |
| 20 | 56 | metastatic | abdomen/retroperitoneum (prior endometrial primary) | N/A | N/A | no | no |
| 21 | 55 | Primary | Uterus endometrium | Present | 30% | No | yes |

N/A = Not applicable.
HRT = hormone replacement therapy

Karyotypes were successfully obtained in 14/21 cases (67%) and nine (43%) exhibited chromosomal aberrations (Table 6). Two of these (one primary MA with SO [case 19] and one metastatic MA [case 20]) had markedly complex karyotypes, displaying extreme aneuploidy with numerous rearrangements (FIG. 8). Seven (two primary MA without SO, three primary MA with SO, and two metastatic MA) demonstrated non-complex clonal aberrations in one or more chromosomes, of which five (71%) included an abnormality involving chromosome 8. Two cases had rearrangements at 8q13 [cases 14 and 16; FIGS. 9A-9B] and three had extra copies of chromosome 8 [cases 15 and 18], one of which also had a translocation involving 8p32. Other chromosomal rearrangements included der(4)t(1; 4)(q21;q35) (case 13), t(11; 21)(q25;q11.2) (case 14), an inversion on chromosome 9 (inv(9)(p22q13)) (case 15), an inversion on chromosome 1 (inv(1)(p36q12)) (case 21), del(14)(q24) (case 21), and t(16; 20)(p13;p11.2) (case 21).

TABLE 6

Cytogenetic aberrations identified using conventional karyotype analysis

| Case # | sample type | Karyotype |
|---|---|---|
| 1 | MA | Not obtained. |
| 2 | MA | Not obtained. |
| 3 | METSO | Not obtained. |
| 4 | METSO | Not obtained. |
| 5 | MASO | Not obtained. |
| 6 | MASO | Not obtained. |
| 7 | MA | Not obtained. |
| 8 | MASO | 46, XX. |
| 9 | METSO | 46, XX. |
| 10 | MASO | 46, XX. |
| 11 | MA | 46, XX. |
| 12 | MA | 46, XX. |
| 13 | MASO | 46, XX, der(4)t(1; 4)(q21; q35)[cp15]. |
| 14 | MA | 46, XX, add(8)(q13), add(8)(q13), t(11; 21)(q25; q11.2)[cp5]/46, XX [cp10]. |
| 15 | MASO | 45-47, X, −X, add(1)(p21), +8, der(8)t(1; 8)(p32; p23), inv(9)(p22q13), +12, −15, −16, +17, ?inv(19)c, −20, +r[cp7]. |
| 16 | METSO | 44, X, del(X)(q24), add(2)(q37), add(5)(p15), del(8)(q13q22), −11, del(14)(q11.2q24), −20[cp14]. |
| 17 | MA | 40-46, XX, +mar[cp5]/46, XX[cp2]. |
| 18 | METSO | 51~56, XX, +del(1)(p12), +5, +7, +8, +8, +i(13)(q10), +15, +21. |
| 19 | MASO | 74-84, XX, complex karyotype[cp6]/46, XX[cp6]. |
| 20 | METSO | 70-80, XX, complex karyotype. |
| 21 | MASO | 47-50, XX, inv(1)(p36q12), +2, +8, +8, del(14)(q24), ?t(16; 20)(p13; p11.2)[cp15]. |

Underlined = same subject
MA = Primary Mullerian adenosarcoma;
MASO = Primary Mullerian adenosarcoma with sarcomatous overgrowth;
METSO = Metastatic sarcoma from a primary uterine mullerian adenosarcoma.

Figure 10:
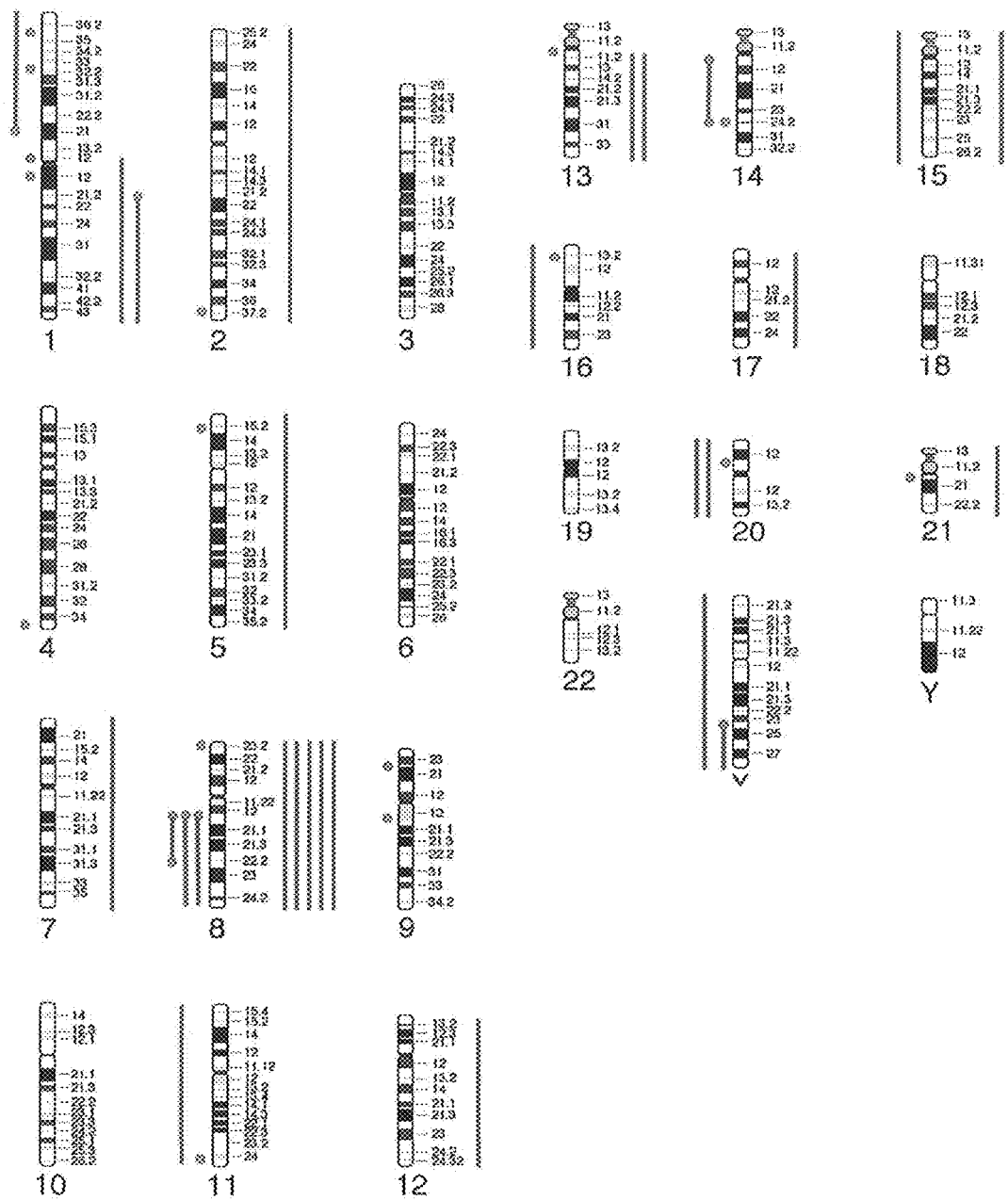
FIG. 10. Graphic summary of all of the cytogenetic findings including tetrasomies, trisomies, monosomies, and rearrangements across all seven cases with non-complex, clonal abnormal karyotypes.

One case (case 17) had an unidentified marker chromosome as the sole aberration. Cases 18 and 21 had tetrasomy of chromosome 8 as well as multiple trisomies including chromosomes 5, 7, 15, and 21 (case 18) and chromosome 2 (case 21). Case 15 had trisomy 8, 12, and 17, monosomy 15, 16, 20, and loss of one X chromosome, and a ring chromosome of uncertain origin. Case 16 also had monosomies 11 and 20 in addition to loss of one X chromosome. FIG. 10 represents a simplified summary of all of the cytogenetic aberrations including trisomies, monosomies, and rearrangements across all cases. Five karyotypes were normal (46, XX) and corresponded to two primary MA without SO, two MA with SO, and one metastatic MA. These cases may represent sampling or growth of non-tumor tissue (e.g., perivascular fibroblasts or accompanying benign epithelial cells) or alternatively, tumors with a normal karyotype.

REFERENCES

1. Clement P B, Scully R E. Mullerian Adenosarcoma of the Uterus. A Clinicopathologic Analysis of Ten Cases of a Distinctive Type of Mullerian Mixed Tumor. *Cancer.* 1974; 34:1138-1149.
2. Clement P B, Scully R E. Mullerian Adenosarcoma of the Uterus: A Clinicopathologic Analysis of 100 Cases with a Review of the Literature. *Hum Pathol.* 1990; 21:363-381.
3. Eichhorn J H, Young R H, Clement P B, et al. Mesodermal (Mullerian) Adenosarcoma of the Ovary: A Clinicopathologic Analysis of 40 Cases and a Review of the Literature. *Am J Surg Pathol.* 2002; 26:1243-1258.
4. Kurman R, Carcangiu M L, Young R H, (Eds). *World Health Organization Classification of Tumours of Female Reproductive Organs*. Lyon: IARC Press; 2014.
5. McCluggage W G. Mullerian Adenosarcoma of the Female Genital Tract. *Adv Anat Pathol.* 2010; 17:122-129.
6. Zaloudek C J, Norris H J. Adenofibroma and Adenosarcoma of the Uterus: A Clinicopathologic Study of 35 Cases. *Cancer.* 1981; 48:354-366.
7. Kaku T, Silverberg S G, Major F J, et al. Adenosarcoma of the Uterus: A Gynecologic Oncology Group Clinicopathologic Study of 31 Cases. *Int J Gynecol Pathol.* 1992; 11:75-88.
8. Amant F, Schurmans K, Steenkiste E, et al. Immunohistochemical Determination of Estrogen and Progesterone Receptor Positivity in Uterine Adenosarcoma. *Gynecol Oncol.* 2004; 93:680-685.
9. Amant F, Steenkiste E, Schurmans K, et al. Immunohistochemical Expression of Cd10 Antigen in Uterine Adenosarcoma. *Int J Gynecol Cancer.* 2004; 14:1118-1121.
10. Auerbach H E, LiVolsi V A, Merino M J. Malignant Mixed Mullerian Tumors of the Uterus. An Immunohistochemical Study. *Int J Gynecol Pathol.* 1988; 7:123-130.
11. Gallardo A, Prat J. Mullerian Adenosarcoma: A Clinicopathologic and Immunohistochemical Study of 55 Cases Challenging the Existence of Adenofibroma. *Am J Surg Pathol.* 2009; 33:278-288.
12. Soslow R A, Ali A, Oliva E. Mullerian Adenosarcomas: An Immunophenotypic Analysis of 35 Cases. *Am J Surg Pathol.* 2008; 32:1013-1021.
13. Abeler V M, Nenodovic M. Diagnostic Immunohistochemistry in Uterine Sarcomas: A Study of 397 Cases. *Int J Gynecol Pathol.* 2011; 30:236-243.
14. Mikami Y, Hata S, Kiyokawa T, et al. Expression of Cd10 in Malignant Mullerian Mixed Tumors and Adenosarcomas: An Immunohistochemical Study. *Mod Pathol.* 2002; 15:923-930.
15. Blom R, Guerrieri C. Adenosarcoma of the Uterus: A Clinicopathologic, DNA Flow Cytometric, P53 and Mdm-2 Analysis of 11 Cases. *Int J Gynecol Cancer.* 1999; 9:37-43.
16. Swisher E M, Gown A M, Skelly M, et al. The Expression of Epidermal Growth Factor Receptor, Her-2/Neu, P53, and Ki-67 Antigen in Uterine Malignant Mixed Mesodermal Tumors and Adenosarcoma. *Gynecol Oncol.* 1996; 60:81-88.
17. Cibulskis K, Lawrence M S, Carter S L, et al. Sensitive Detection of Somatic Point Mutations in Impure and Heterogeneous Cancer Samples. *Nat Biotechnol.* 2013; 31:213-219.
18. McKenna A, Hanna M, Banks E, et al. The Genome Analysis Toolkit: A Mapreduce Framework for Analyzing Next-Generation DNA Sequencing Data. *Genome Res.* 2010; 20:1297-1303.
19. DePristo M A, Banks E, Poplin R, et al. A Framework for Variation Discovery and Genotyping Using Next-Generation DNA Sequencing Data. *Nat Genet.* 2011; 43:491-498.
20. Van der Auwera G A, Carneiro M O, Hartl C, et al. From Fastq Data to High-Confidence Variant Calls: The Genome Analysis Toolkit Best Practices Pipeline. *Current Protocols in Bioinformatics*: John Wiley & Sons, Inc.; 2013.
21. Garcia E P K F, Jia Y, Zepf D, Crosby L. Development and Clinical Validation of a Targeted Next-Generation Sequencing Platform for the Detection of Somatic Mutations, Indels, Rearrangements, and Copy-Number Alterations in Human Tumors. *The Journal of Molecular Diagnostics.* 2013; 15:872.
22. Spencer D H, Sehn J K, Abel H J, et al. Comparison of Clinical Targeted Next-Generation Sequence Data from Formalin-Fixed and Fresh-Frozen Tissue Specimens. *J Mol Diagn.* 2013; 15:623-633.
23. Marinoni I, Kurrer A S, Vassella E, et al. Loss of Daxx and Atrx Are Associated with Chromosome Instability and Reduced Survival of Patients with Pancreatic Neuroendocrine Tumors. *Gastroenterology.* 2014; 146:453-460 e455.
24. de Wilde R F, Heaphy C M, Maitra A, et al. Loss of Atrx or Daxx Expression and Concomitant Acquisition of the Alternative Lengthening of Telomeres Phenotype Are Late Events in a Small Subset of Men-1 Syndrome Pancreatic Neuroendocrine Tumors. *Mod Pathol.* 2012; 25:1033-1039.
25. Krivak T C, Seidman J D, McBroom J W, et al. Uterine Adenosarcoma with Sarcomatous Overgrowth Versus Uterine Carcinosarcoma: Comparison of Treatment and Survival. *Gynecol Oncol.* 2001; 83:89-94.
26. Kobayashi H, Uekuri C, Akasaka J, et al. The Biology of Uterine Sarcomas: A Review and Update. *Mol Clin Oncol.* 2013; 1:599-609.
27. Gollard R, Kosty M, Bordin G, et al. Two Unusual Presentations of Mullerian Adenosarcoma: Case Reports, Literature Review, and Treatment Considerations. *Gynecol Oncol.* 1995; 59:412-422.
28. Bernard B, Clarke B A, Malowany J I, et al. Uterine Adenosarcomas: A Dual-Institution Update on Staging, Prognosis and Survival. *Gynecol Oncol.* 2013; 131:634-639.
29. Fox H, Harilal K R, Youell A. Mullerian Adenosarcoma of the Uterine Body: A Report of Nine Cases. *Histopathology.* 1979; 3:167-180.
30. Manoharan M, Azmi M A, Soosay G, et al. Mullerian Adenosarcoma of Uterine Cervix: Report of Three Cases and Review of Literature. *Gynecol Oncol.* 2007; 105:256-260.
31. Van Mieghem T, Abeler V M, Moerman P, et al. Cd10, Estrogen and Progesterone Receptor Expression in Ovarian Adenosarcoma. *Gynecol Oncol.* 2005; 99:493-496.
32. Taylor N P, Zighelboim I, Huettner P C, et al. DNA Mismatch Repair and Tp53 Defects Are Early Events in Uterine Carcinosarcoma Tumorigenesis. *Mod Pathol.* 2006; 19:1333-1338.
33. Anderson S E, Nonaka D, Chuai S, et al. P53, Epidermal Growth Factor, and Platelet-Derived Growth 34. Liu F S, Kohler M F, Marks J R, et al. Mutation and Overexpression of the P53 Tumor Suppressor Gene Frequently Occurs in Uterine and Ovarian Sarcomas. *Obstet Gynecol*. 1994; 83:118-124.

35. Ito M, Barys L, O'Reilly T, et al. Comprehensive Mapping of P53 Pathway Alterations Reveals an Apparent Role for Both Snp309 and Mdm2 Amplification in Sarcomagenesis. *Clin Cancer Res*. 2011; 17:416-426.

36. Sprogoe-Jakobsen S, Holund B. Immunohistochemistry (Ki-67 and P53) as a Tool in Determining Malignancy in Smooth Muscle Neoplasms (Exemplified by a Myxoid Leiomyosarcoma of the Uterus). *APMIS*. 1996; 104:705-708.

37. Jiao Y, Killela P J, Reitman Z J, et al. Frequent Atrx, Cic, Fubpl and Idhl Mutations Refine the Classification of Malignant Gliomas. *Oncotarget*. 2012; 3:709-722.

38. Wu G, Diaz A K, Paugh B S, et al. The Genomic Landscape of Diffuse Intrinsic Pontine Glioma and Pediatric Non-Brainstem High-Grade Glioma. *Nat Genet*. 2014; 46:444-450.

39. Jiao Y, Shi C, Edil B H, et al. Daxx/Atrx, Menl, and Mtor Pathway Genes Are Frequently Altered in Pancreatic Neuroendocrine Tumors. *Science*. 2011; 331:1199-1203.

40. Ramkissoon L A, Horowitz P M, Craig J M, et al. Genomic Analysis of Diffuse Pediatric Low-Grade Gliomas Identifies Recurrent Oncogenic Truncating Rearrangements in the Transcription Factor Mybl1. *Proc Natl Acad Sci USA*. 2013; 110:8188-8193.

41. Chen Z, Hong B, Drozd-Borysiuk E, et al. Molecular Cytogenetic Characterization of a Case of Mullerian Adenosarcoma. *Cancer Genet Cytogenet*. 2004; 148:129-132.

42. Dei Tos A P, Doglioni C, Piccinin S, et al. Molecular Abnormalities of the P53 Pathway in Dedifferentiated Liposarcoma. *J Pathol*. 1997; 181:8-13.

43. Maekawa Y, Tsukumo S, Chiba S, et al. Deltal-Notch3 Interactions Bias the Functional Differentiation of Activated Cd4+ T Cells. *Immunity*. 2003; 19:549-559.

44. Tallini G, Vanni R, Manfioletti G, et al. Hmgi-C and Hmgi(Y) Immunoreactivity Correlates with Cytogenetic Abnormalities in Lipomas, Pulmonary Chondroid Hamartomas, Endometrial Polyps, and Uterine Leiomyomas and Is Compatible with Rearrangement of the Hmgi-C and Hmgi(Y) Genes. *Lab Invest*. 2000; 80:359-369.

45. Dal Cin P, Timmerman D, Van den Berghe I, et al. Genomic Changes in Endometrial Polyps Associated with Tamoxifen Show No Evidence for Its Action as an External Carcinogen. *Cancer Res*. 1998; 58:2278-2281.

46. Dal Cin P, Van Den Berghe H, Brosens I. Involvement of 6p in an Endometrial Polyp. *Cancer Genet Cytogenet*. 1991; 51:279-280.

47. Dal Cin P, Vanni R, Marras S, et al. Four Cytogenetic Subgroups Can Be Identified in Endometrial Polyps. *Cancer Res*. 1995; 55:1565-1568.

48. Vanni R, Dal Cin P, Marras S, et al. Endometrial Polyp: Another Benign Tumor Characterized by 12q13-Q15 Changes. *Cancer Genet Cytogenet*. 1993; 68:32-33.

49. Bol S, Wanschura S, Thode B, et al. An Endometrial Polyp with a Rearrangement of Hmgi-C Underlying a Complex Cytogenetic Rearrangement Involving Chromosomes 2 and 12. *Cancer Genet Cytogenet*. 1996; 90:88-90.

50. Walter T A, Fan S X, Medchill M T, et al. Inv(12) (P11.2q13) in an Endometrial Polyp. *Cancer Genet Cytogenet*. 1989; 41:99-103.

51. Speleman F, Dal Cin P, Van Roy N, et al. Is T(6; 20)(P21;Q13) a Characteristic Chromosome Change in Endometrial Polyps? *Genes Chromosomes Cancer*. 1991; 3:318-319.

52. Medeiros F, Erickson-Johnson M R, Keeney G L, et al. Frequency and Characterization of Hmga2 and Hmga1 Rearrangements in Mesenchymal Tumors of the Lower Genital Tract. *Genes Chromosomes Cancer*. 2007; 46:981-990.

53. Nucci M R, Weremowicz S, Neskey D M, et al. Chromosomal Translocation T(8; 12) Induces Aberrant Hmgic Expression in Aggressive Angiomyxoma of the Vulva. *Genes Chromosomes Cancer*. 2001; 32:172-176.

54. Medeiros F, Araujo A R, Erickson-Johnson M R, et al. Hmga1 and Hmga2 Rearrangements in Mass-Forming Endometriosis. *Genes Chromosomes Cancer*. 2010; 49:630-634.

55. Dal Cin P, Kools P, De Jonge I, et al. Rearrangement of 12q14-15 in Pulmonary Chondroid Hamartoma. *Genes Chromosomes Cancer*. 1993; 8:131-133.

56. Dal Cin P, Turc-Carel C, Sandberg A A. Consistent Involvement of Band 12q14 in Two Different Translocations in Three Lipomas from the Same Patient. *Cancer Genet Cytogenet*. 1988; 31:237-240.

57. Dal Cin P, Wanschura S, Kazmierczak B, et al. Amplification and Expression of the Hmgic Gene in a Benign Endometrial Polyp. *Genes Chromosomes Cancer*. 1998; 22:95-99.

58. Tesfaye A, Di Cello F, Hillion J, et al. The High-Mobility Group A1 Gene up-Regulates Cyclooxygenase 2 Expression in Uterine Tumorigenesis. *Cancer Res*. 2007; 67:3998-4004.

59. Boo L M, Lin H H, Chung V, et al. High Mobility Group A2 Potentiates Genotoxic Stress in Part through the Modulation of Basal and DNA Damage-Dependent Phosphatidylinositol 3-Kinase-Related Protein Kinase Activation. *Cancer Res*. 2005; 65:6622-6630.

Abeler, V. M., 0. Royne, S. Thoresen, H. E. Danielsen, J. M. Nesland and G. B. Kristensen (2009). "Uterine sarcomas in Norway. A histopathological and prognostic survey of a total population from 1970 to 2000 including 419 patients." Histopathology 54(3): 355-364.

Chiang, S. and E. Oliva (2011). "Cytogenetic and molecular aberrations in endometrial stromal tumors." Hum Pathol 42(5): 609-617.

Clappier, E., W. Cuccuini, A. Kalota, A. Crinquette, J. M. Cayuela, W. A. Dik, A. W. Langerak, B. Montpellier, B. Nadel, P. Walrafen, O. Delattre, A. Aurias, T. Leblanc, H. Dombret, A. M. Gewirtz, A. Baruchel, F. Sigaux and J. Soulier (2007). "The C-MYB locus is involved in chromosomal translocation and genomic duplications in human T-cell acute leukemia (T-ALL), the translocation defining a new T-ALL subtype in very young children." Blood 110(4): 1251-1261.

Clement, P. B. (1989). "Mullerian adenosarcomas of the uterus with sarcomatous overgrowth. A clinicopathological analysis of 10 cases." Am J Surg Pathol 13(1): 28-38.

Clement, P. B. and R. E. Scully (1978). "Extrauterine mesodermal (mullerian) adenosarcoma: a clinicopathologic analysis of five cases." Am J Clin Pathol 69(3): 276-283.

Dewaele B, Przybyl J, Quattrone A, Finalet Ferreiro J, Vanspauwen V, Geerdens E, Gianfelici V, Kalender Z, Wozniak A, Moerman P, Sciot R, Croce S, Amant F, Vandenberghe P, Cools J, Debiec-Rychter M. "Identification of a novel, recurrent MBTD1-CXorf67 fusion in low-grade endometrial stromal sarcoma." Int J Cancer 134(5): 1112-22.

Jones, M. W. and M. Lefkowitz (1995). "Adenosarcoma of the uterine cervix: a clinicopathological study of 12 cases." Int J Gynecol Pathol 14(3): 223-229.

Laxman, R., J. L. Currie, R. J. Kurman, M. Dudzinski and C. A. Griffin (1993). "Cytogenetic profile of uterine sarcomas." Cancer 71(4): 1283-1288.

Major, F. J., J. A. Blessing, S. G. Silverberg, C. P. Morrow, W. T. Creasman, J. L. Currie, E. Yordan and M. F. Brady (1993). "Prognostic factors in early-stage uterine sarcoma. A Gynecologic Oncology Group study." Cancer 71(4 Suppl): 1702-1709.

Mitani, Y., J. Li, P. H. Rao, Y. J. Zhao, D. Bell, S. M. Lippman, R. S. Weber, C. Caulin and A. K. El-Naggar (2010). "Comprehensive analysis of the MYB-NFIB gene fusion in salivary adenoid cystic carcinoma: Incidence, variability, and clinicopathologic significance." Clin Cancer Res 16(19): 4722-4731.

West, R. B., C. Kong, N. Clarke, T. Gilks, J. S. Lipsick, H. Cao, S. Kwok, K. D. Montgomery, S. Varma and Q. T. Le (2011). "MYB expression and translocation in adenoid cystic carcinomas and other salivary gland tumors with clinicopathologic correlation." Am J Surg Pathol 35(1): 92-99.

Zhang, et al., (2013). "Whole-genome sequencing identifies genetic alterations in pediatric low-grade gliomas." Nat Genet 45(6): 602-612.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has Müllerian Adenosarcoma (MA), the method comprising:
   obtaining a sample comprising cells from the MA in a subject;
   performing an assay to determine the copy number of each of a MYBL1, MDM2, and CDK4 gene;
   comparing the copy number of the MYBL1, MDM2, and CDK4 genes to reference copy number that represents a copy number in a normal cell;
   detecting a copy number gain in a MYBL1, MDM2, or CDK4 gene as compared to the reference copy number; and
   administering to a subject who has a copy number gain or loss in a MYBL1 or CDK4 gene, or a copy number gain in a MDM2 gene as compared to the reference copy number a treatment comprising one or more of radical surgical resection; administration of radiotherapy; or administration of chemotherapy.

2. The method of claim 1, wherein performing an assay to determine the copy number of a gene comprises using a method selected from the group consisting of fluorescent in-situ hybridization (FISH); gene chip hybridization; multiplexed gene expression analysis; hybridization based digital barcode quantification assays; and lysate based hybridization assays utilizing branched DNA signal amplification.

3. A method of treating a subject who has Mullerian Adenosarcoma (MA), the method comprising:
   obtaining a sample comprising cells from the MA in the subject;
   performing an assay to determine copy number of a MYBL1 gene;
   comparing the copy number of the MYBL1 gene to a reference copy number that represents a MYBL1 copy number in a normal cell;
   detecting a copy number gain in MYBL1 gene as compared to the reference copy number; and
   administering to a subject who has a copy number gain in a MYBL1 gene as compared to the reference copy number a treatment comprising an MYBL1 inhibitor, wherein the MYBL1 inhibitor is mexicanin I.

4. The method of claim 1, wherein the mass is a uterine or cervical mass, and the radical surgical resection is radical hysterectomy or modified radical hysterectomy.

5. The method of claim 2, wherein determining the copy number of the MYBL1 a gene comprises using a method selected from the group consisting of fluorescent in-situ hybridization (FISH); gene chip hybridization; multiplexed gene expression analysis; hybridization based digital barcode quantification assays; and lysate based hybridization assays utilizing branched DNA signal amplification.

* * * * *

UNITED STATES PATENT AND TRADEMARK OFFICE
CERTIFICATE OF CORRECTION

PATENT NO. : 10,119,169 B2
APPLICATION NO. : 14/685292
DATED : November 6, 2018
INVENTOR(S) : Brooke Howitt et al.

Page 1 of 1

It is certified that error appears in the above-identified patent and that said Letters Patent is hereby corrected as shown below:

In the Claims

In Column 42, Line 37 (approx.), Claim 5, delete "claim 2," and insert -- claim 3, --

Signed and Sealed this
Twenty-eighth Day of May, 2019

Andrei Iancu
*Director of the United States Patent and Trademark Office*